United States Patent
Kawagishi et al.

(10) Patent No.: US 7,303,529 B2
(45) Date of Patent: Dec. 4, 2007

(54) ULTRASONIC DIAGNOSTIC EQUIPMENT AND ULTRASONIC IMAGE GENERATION METHOD

(75) Inventors: Tetsuya Kawagishi, Kuroiso (JP); Tomohisa Imamura, Tochigi-ken (JP); Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 369 days.

(21) Appl. No.: 10/798,353

(22) Filed: Mar. 12, 2004

(65) Prior Publication Data

US 2004/0254462 A1 Dec. 16, 2004

(30) Foreign Application Priority Data

Mar. 14, 2003 (JP) ............................. 2003-070935
Mar. 10, 2004 (JP) ............................. 2004-067850

(51) Int. Cl.
*A61B 8/00* (2006.01)

(52) U.S. Cl. ...................................... 600/443; 600/458
(58) Field of Classification Search ................ 600/437, 600/439, 443–447, 458, 462–463; 73/625–626; 128/916
See application file for complete search history.

(56) References Cited

U.S. PATENT DOCUMENTS

| | | | | |
|---|---|---|---|---|
| 3,816,753 | A * | 6/1974 | Kino | 359/330 |
| 4,844,082 | A * | 7/1989 | Fukukita et al. | 600/442 |
| 5,521,882 | A * | 5/1996 | D'Angelo et al. | 367/32 |
| 6,117,082 | A * | 9/2000 | Bradley et al. | 600/447 |
| 6,440,075 | B1 * | 8/2002 | Averkiou | 600/443 |
| 6,458,084 | B2 * | 10/2002 | Tsao et al. | 600/443 |
| 6,705,996 | B2 | 3/2004 | Kawagishi et al. | |
| 6,953,434 | B2 * | 10/2005 | Hao et al. | 600/458 |
| 6,960,169 | B2 * | 11/2005 | Mao et al. | 600/458 |
| 7,056,290 | B2 * | 6/2006 | Rielly et al. | 600/447 |
| 7,074,186 | B2 * | 7/2006 | Loftman et al. | 600/437 |
| 2007/0167780 | A1 | 7/2007 | Imamura et al. | |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

The difference frequency component between a first fundamental wave of frequency $f$ and a second fundamental wave of frequency $f_2$ is caused to interact with a second harmonic wave, thereby to attain the enhancement of a second harmonic signal, etc., whereby a reflected wave component to be imaged is extracted at a high S/N ratio. By way of example, in a case where the difference frequency component is to appear on the lower frequency side of the second harmonic wave of the first fundamental wave so as to be superposed on this second harmonic wave, the frequencies are set at $f_2=2.8f$ or so. Besides, in a case where the difference frequency component is to appear on the higher frequency side of the second harmonic wave of the first fundamental wave so as to be superposed on this second harmonic wave, the frequencies are set at $f_2=3.2f$ or so.

9 Claims, 17 Drawing Sheets

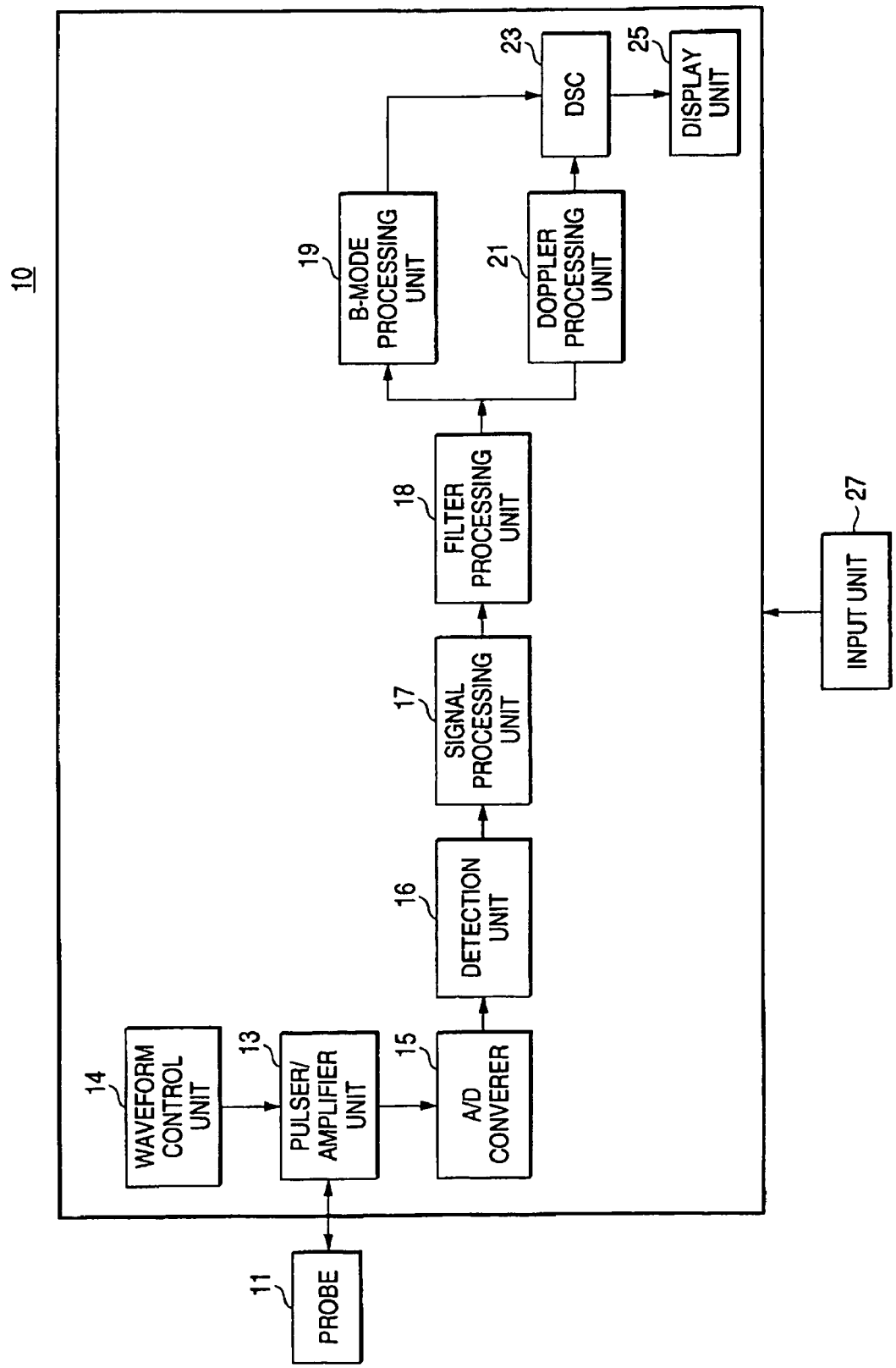

TRANSMISSION FREQUENCY

RECEPTION FREQUENCY (1) RECEIVED SECOND HARMONIC WAVE (2) RECEIVED DIFFERENCE FREQUENCY COMPONENT (1) + (2) (REFLECTED WAVE COMPONENT OBSERVED IN VICINITY OF 2f)

(1) RECEIVED SECOND HARMONIC WAVE (2) RECEIVED DIFFERENCE FREQUENCY COMPONENT (1) + (2) (REFLECTED WAVE COMPONENT OBSERVED IN VICINITY OF 2f)

(1) RECEIVED SECOND HARMONIC WAVE (2) RECEIVED DIFFERENCE FREQUENCY COMPONENT (1) + (2) (REFLECTED WAVE COMPONENT OBSERVED IN VICINITY OF 2f)

(1) RECEIVED SECOND HARMONIC WAVE (2) RECEIVED DIFFERENCE FREQUENCY COMPONENT AND SUM FREQUENCY COMPONENT (1) + (2)

(1) RECEIVED SECOND HARMONIC WAVE (2) RECEIVED DIFFERENCE FREQUENCY COMPONENT AND SUM FREQUENCY COMPONENT (1) + (2)

NOISE COMPONENT

NOISE COMPONENT
(LEAKAGE COMPONENT OF FUNDAMENTAL WAVE)

NOISE COMPONENT
(LEAKAGE COMPONENT OF FUNDAMENTAL WAVE)

ULTRASONIC DIAGNOSTIC EQUIPMENT AND ULTRASONIC IMAGE GENERATION METHOD

CROSS-REFERENCE TO RELATED APPLICATIONS

This application is based upon and claims the benefit of priority from prior Japanese Patent Applications No. 2003-070935, filed Mar. 14, 2003; and No. 2004-067850, filed Mar. 10, 2004, the entire contents of both of which are incorporated herein by reference.

BACKGROUND OF THE INVENTION

1. Field of the Invention

The present invention relates to an ultrasonic diagnostic equipment for use in the fields of medical care, etc., and more particularly to video technology utilizing a nonlinear phenomenon.

2. Description of the Related Art

An ultrasonic diagnostic equipment is a medical image equipment with which the tomographic image of a soft tissue in a living body is noninvasively obtained from the surface of the body by the ultrasonic pulse echo method. As compared with other medical image equipment, the ultrasonic diagnostic equipment has such merits as being small-sized and inexpensive, affording a high safety without exposure to X-rays etc., and being capable of blood flow imaging, and it is extensively utilized for the heart, the abdomen and the urinary organs and in obstetrics and gynecology, etc.

In the ultrasonic image diagnostic equipment, bio-information can be imaged by various imaging methods. The contrast echo method, for example, gives an ultrasonic contrast medium made of microbubbles or the likes, into the blood vessel of a patient, thereby to attain the enhancement of an ultrasonic scattering echo. In such an imaging method, it has hitherto been an important problem to extract an echo signal component to-be-imaged at a high S/N ratio from a received signal. Therefore, various contrivances have been made in the respective imaging methods.

Concretely, in second harmonic imaging, the band of a second harmonic wave to-be-imaged is determined by that of a fundamental wave. Accordingly, the bandwidth of the second harmonic wave is controlled by adjusting the fundamental wave band, so as to obtain a signal suitable for the imaging. By way of example, in order to broaden the second harmonic wave onto a lower frequency side, the fundamental wave may, in principle, be broadened onto the lower frequency side. Besides, in case of broadening the second harmonic wave onto a higher frequency side, the fundamental wave may be broadened onto the higher frequency side.

In actuality, however, the band of the fundamental wave as can be broadened onto the lower frequency side is limited by a probe band as shown in FIG. 1A. Besides, in a case where the second harmonic wave has been broadened onto the higher frequency band, the bands of the fundamental wave and the second harmonic wave overlap each other in the received signal as shown in FIG. 1A, so that separation into the respective bands is sometimes difficult.

Besides, in the contrast echo, when a band intermediate between the fundamental wave and the second harmonic wave is imaged, the contrast between the tissue and the contrast medium can be heightened.

However, it is difficult to completely remove the fundamental wave and the second harmonic wave at all times, and in the case where the intermediate band has been imaged, it is sometimes impossible to offer appropriate bio-information. By way of example, in a case where the vicinity of a 1.5$f_0$ band is imaged as shown in FIG. 1B, it can occur that parts of both the waves enter the band to-be-imaged, and that a tissue exhibiting a high echo is imaged together in the contrasting mode, to make the judgment of contrast difficult.

BRIEF SUMMARY OF THE INVENTION

The present invention has been made in view of the above circumstances, and has for its object to provide an ultrasonic diagnostic equipment and an ultrasonic image generation method in which a difference frequency component and a second harmonic component are caused to interact by controlling the phase of the difference frequency component, etc., whereby a reflected wave component to-be-imaged is extracted at a high accuracy.

The present invention may provide an ultrasonic diagnostic equipment comprising a transmission ultrasonic wave generation unit which generates a transmission ultrasonic wave that has, at least, a first fundamental wave, and a second fundamental wave at a frequency higher than that of the first fundamental wave, and which generates the transmission ultrasonic wave by controlling the frequency of at least one of the first and second fundamental waves in order that, in case of transmitting the transmission ultrasonic wave to a patient and receiving a reflected wave therefrom, a difference frequency component between the first fundamental wave and the second fundamental wave as is included in the reflected wave may interact with a second harmonic wave of the first fundamental wave, and also by controlling a phase of at least one of the first and second fundamental waves in order to control the interaction; a transmission unit which transmits the transmission ultrasonic wave to the patient; a reception unit which receives the reflected wave of the transmission ultrasonic wave from the patient; and an image generation unit which generates an ultrasonic image on the basis of the reflected wave.

The present invention may provide an ultrasonic diagnostic equipment comprising a transmission ultrasonic wave generation unit which generates a transmission ultrasonic wave that has, at least, a first fundamental wave, and a second fundamental wave at a frequency higher than that of the first fundamental wave, and which generates the transmission ultrasonic wave by controlling the frequency of at least one of the first and second fundamental waves in order that, in case of transmitting the transmission ultrasonic wave to a patient and receiving a reflected wave therefrom, a sum frequency component between the first fundamental wave and the second fundamental wave as is included in the reflected wave may interact with at least one of a second harmonic wave of the first fundamental wave and a second harmonic wave of the second fundamental wave, and also by controlling a phase of at least one of the first and second fundamental waves in order to control the interaction; a transmission unit which transmits the transmission ultrasonic wave to the patient; a reception unit which receives the reflected wave of the transmission ultrasonic wave from the patient; and an image generation unit which generates an ultrasonic image on the basis of the reflected wave.

The present invention may provide an ultrasonic diagnostic equipment comprising a transmission ultrasonic wave generation unit which generates a transmission ultrasonic wave that has, at least, a first fundamental wave, and a second fundamental wave at a frequency higher than that of the first fundamental wave, and which generates the transmission ultrasonic wave by controlling a phase of at least the second fundamental wave in order that, in case of transmitting the transmission ultrasonic wave to a patient and receiving a reflected wave therefrom, a difference frequency component or a sum frequency component between the first fundamental wave and the second fundamental wave as is included in the reflected wave may cancel leakage of at least one of the first and second fundamental waves; a transmission unit which transmits the transmission ultrasonic wave to the patient; a reception unit which receives the reflected wave of the transmission ultrasonic wave from the patient; and an image generation unit which generates an ultrasonic image on the basis of the reflected wave.

The present invention may provide an ultrasonic image generation method comprising generating a transmission ultrasonic wave that has, at least, a first fundamental wave, and a second fundamental wave at a frequency higher than that of the first fundamental wave, by controlling the frequency of at least one of the first and second fundamental waves in order that, in case of transmitting the transmission ultrasonic wave to a patient and receiving a reflected wave therefrom, a difference frequency component between the first fundamental wave and the second fundamental wave as is included in the reflected wave may interact with a second harmonic wave of the first fundamental wave, and also by controlling a phase of at least one of the first and second fundamental waves in order to control the interaction; transmitting the transmission ultrasonic wave to the patient; receiving the reflected wave of the transmission ultrasonic wave from the patient; and generating an ultrasonic image on the basis of the reflected wave.

The present invention may provide an ultrasonic image generation method comprising generating a transmission ultrasonic wave that has, at least, a first fundamental wave, and a second fundamental wave at a frequency higher than that of the first fundamental wave, by controlling the frequency of at least one of the first and second fundamental waves in order that, in case of transmitting the transmission ultrasonic wave to a patient and receiving a reflected wave therefrom, a sum frequency component between the first fundamental wave and the second fundamental wave as is included in the reflected wave may interact with at least one of a second harmonic wave of the first fundamental wave and a second harmonic wave of the second fundamental wave, and also by controlling a phase of at least one of the first and second fundamental waves in order to control the interaction; transmitting the transmission ultrasonic wave to the patient; receiving the reflected wave of the transmission ultrasonic wave from the patient; and generating an ultrasonic image on the basis of the reflected wave.

The present invention may provide an ultrasonic image generation method comprising generating a transmission ultrasonic wave that has, at least, a first fundamental wave, and a second fundamental wave at a frequency higher than that of the first fundamental wave, by controlling a phase of at least the second fundamental wave in order that, in case of transmitting the transmission ultrasonic wave to a patient and receiving a reflected wave therefrom, a difference frequency component or a sum frequency component between the first fundamental wave and the second fundamental wave as is included in the reflected wave may cancel leakage of at least one of the first and second fundamental waves; transmitting the transmission ultrasonic wave to the patient; receiving the reflected wave of the transmission ultrasonic wave from the patient; and generating an ultrasonic image on the basis of the reflected wave.

BRIEF DESCRIPTION OF THE VIEWS OF THE DRAWING

FIG. 2A is a diagram showing the layout of an ultrasonic diagnostic equipment 10 according to a first embodiment;

DETAILED DESCRIPTION OF THE INVENTION

Figure 1A:
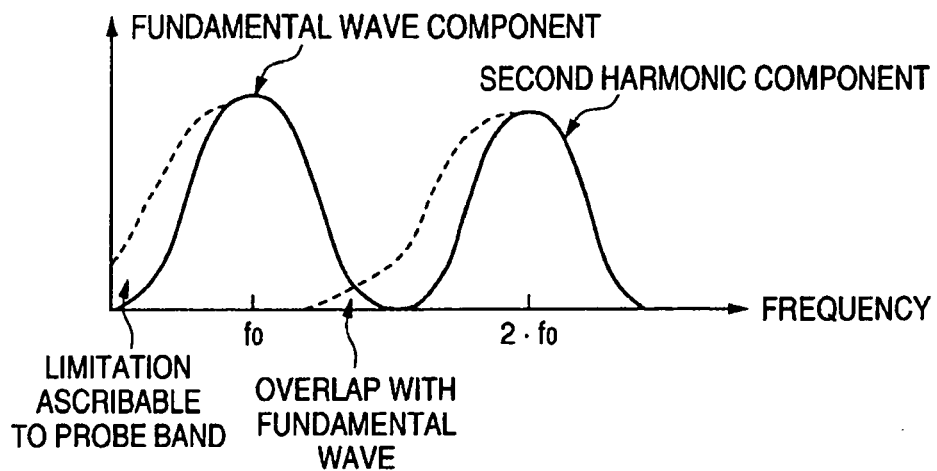
FIG. 1A is a diagram for explaining the prior art.

Now, the first embodiment-fifth embodiment of the present invention will be described in conjunction with the drawings. By the way, in the ensuing description, identical reference numerals and signs will be assigned to constituents which have substantially the same functions and configurations, and they shall be repeatedly explained only in necessary cases.

First Embodiment

First, the layout of an ultrasonic diagnostic equipment 10 according to this embodiment will be described with reference to FIG. 2A. As shown in FIG. 2A, the ultrasonic diagnostic equipment includes an ultrasonic probe 11, a pulser/amplifier unit 13, a waveform control unit 14, an A/D converter 15, a detection unit 16, a signal processing unit 17, a filter processing unit 18, a filter processing unit 18, a B-mode processing unit 19, a Doppler processing unit 21, a DSC 23, a display unit 25, and an input unit 27.

The ultrasonic probe 11 has a plurality of piezoelectric transducers which generate an ultrasonic wave on the basis of a drive signal from the pulser and which convert reflected waves from a patient, into electric signals, matching layers which are disposed for the piezoelectric transducers, a backing material which prevents ultrasonic waves from propagating backwards from the piezoelectric transducers, and so forth. When the ultrasonic wave is transmitted from the ultrasonic probe 11 to the patient, various harmonic components are generated with the propagation of the ultrasonic wave by the nonlinearity of in vivo tissues. A fundamental wave and harmonic components, which constitute the transmission ultrasonic wave, are backscattered by the boundaries of the acoustic impedances of the in vivo tissues, minute scatterers, etc., and the scattered waves are received as reflected waves (echoes) by the ultrasonic probe 11.

In order to form the transmission ultrasonic wave in a transmission mode, the pulser/amplifier unit 13 recurrently generates rate pulses at a predetermined rate frequency of fr Hz (period; 1/fr second) under a control based on the waveform control unit 14, and it focuses the ultrasonic wave into the shape of a beam every channel and gives each rate pulse a delay time necessary for determining a transmission directivity. The pulser/amplifier unit 13 impresses drive pulses on the probe 11 at timings based on the rate pulses.

Besides, the pulser/amplifier unit 13 amplifies an echo signal accepted through the probe 11, every channel in a reception mode. Further, the pulser/amplifier unit 13 gives the amplified echo signal a delay time necessary for determining a reception directivity and then executes addition processing in the reception mode. Owing to the addition, a reflection component which arrives in a direction corresponding to the reception directivity of the echo signal is enhanced, and the overall directivity (scanning line) of the ultrasonic transmission and reception is determined by the reception directivity and the transmission directivity.

By the way, in a case where a digital wave former, for example, is used in the pulse/amplifier unit 13 or the like, so as to determine the waveform of the transmission ultrasonic wave therewith, such processing as compositing intervenes in a series of imaging, and hence, indirect noise (the leakage component of the fundamental wave) sometimes enters into a measured reception signal. The ultrasonic diagnostic equipment 10 is capable of removing the indirect noise. This will be explained in detail later.

The waveform control unit 14 controls the pulser/amplifier unit 13 so as to form the waveform of the transmission ultrasonic wave, which is constituted by, for example, two fundamental waves (first fundamental wave, second fundamental wave), on the basis of an instruction from the input unit 27, a preset program, or the like. More specifically, the waveform control unit 14 controls the physical conditions (such as frequency, amplitude and phase) of the second fundamental wave so that the difference frequency component between the second fundamental wave and the first fundamental wave may appear in the vicinity of the frequency of the second harmonic wave of the first fundamental wave so as to interact with the second harmonic wave (so as to enhance or weaken amplitudes each other, or to give rise to phase interference in which the spectra of the difference frequency component and the second harmonic wave overlap each other).

The A/D converter 15 converts an analog signal received from the pulser/amplifier unit 13, into a digital signal.

The detection unit 16 performs quadrature phase detection in such a way that the signal received from the A/D converter 15 is multiplied by signals having reference frequencies of a phase shift of 90 degrees, respectively, whereby I and Q signals are obtained. The I and Q signals become signals which have frequencies obtained by subtracting the reference frequencies from the received signal. Incidentally, the reference frequencies are generally set at the center frequency of a band in which an ultrasonic image is generated.

The signal processing unit 17 executes such predetermined signal processing as subtraction processing. More specifically, the signal processing unit 17 executes the subtraction processing in the contrast echo after transmitting an ultrasonic wave continuously to one scanning line and receiving a plurality of reception echoes, thereby to erase a tissue image and to extract a contrast medium echo component. Besides, harmonic components except the fundamental wave are extracted using a signal obtained by the phase inversion method.

The filter processing unit 18 is a complex digital filter which attenuates reflected wave components in a predetermined frequency band and extracts (filters) reflected wave components in a desired frequency band, thereby to output the reflected wave components to the B-mode processing unit 19 or the Doppler processing unit 21. In this embodiment, the filter processing unit 18 executes the filtering by way of example so that the reflected wave components in the vicinity of the frequency band of the second harmonic wave corresponding to the first fundamental wave may be, at least, contained.

The B-mode processing unit 19 performs logarithmic amplification, etc. for the received signal subjected to the filter processing. The amplified signal is sent to the DSC 23, and it is color-displayed on the display unit 25 as a B-mode image in which the intensity of a reflected wave is represented by brightness.

The Doppler processing unit 21 extracts a blood flow or tissue and the contrast medium echo component on the basis of the Doppler effect, and finds a mean speed, variance, power, and the like blood flow information at multiple points. The blood flow information items are sent to the DSC 23, and are color-displayed on the display unit 25 as a mean speed image, a variance image, a power image, and an image in which they are combined.

The DSC 23 converts the scanning line signal train of ultrasonic scan inputted from the B-mode processing unit 19 or the Doppler processing unit 21, into the data of a rectangular coordinate system based on spatial information, and it further performs a video format change.

The display unit 25 displays in vivo morphological information or the blood flow information as an image on the basis of the video signal from the DSC 23. Besides, in the case of employing the contrast medium, the display unit 25 displays a brightness image or a color image on the basis of a quantitative information content from which the spatial distribution of the contrast medium, that is, the blood flow or a region where blood exists has been obtained.

The input unit 27 is connected to the body of the equipment 10, and it is furnished with a control (a mouse or track ball, a mode changeover switch, a keyboard, etc.) for the setting of a region of interest (ROI), etc. in order to accept various instructions, commands and information from an operator into the equipment body 22. Besides, the transmission conditions of the transmission ultrasonic wave can also be manually in the vicinity of a frequency 2f. The reflected wave is equivalent to a wave in which the second harmonic wave of the first fundamental wave as has the center frequency of 2f is broadened onto a higher frequency side so as to enlarge its peak.

Difference Frequency Component

Next, there will be described the principle of generating a difference frequency component which is utilized in the imaging method. In general, in a case where a fundamental wave is denoted by $a \cdot \sin ft$, a square nonlinear effect can be expressed as $(a \cdot \sin ft)^2$. Besides, in case of using transmission ultrasonic waves which consist of a first fundamental wave of $\sin f_1 t$ and a second fundamental wave of $a \cdot \sin f_2 t$, the nonlinear effect can be expressed as $(\sin f_1 t + a \cdot \sin f_2 t)^2$, which can be reduced as follows:

$$(\sin f_1 t + a \cdot \sin f_2 t)^2 = (\sin f_1 t)^2 \pm 2a \cdot \sin f_1 t \cdot \sin f_2 t + (a \cdot \sin f_2 t)^2$$
$$= 1/2\{\sin 2 f_1 t \mp a \cdot \sin(f_2 - f_1)t\} + \cdots$$

Here, the first term of the last line is the second harmonic component of the first fundamental wave, and the second term corresponds to the difference frequency component between the second fundamental wave and the first fundamental wave. Besides, fundamental wave components, sum frequency components, etc. are included in terms omitted at the third line.

With the method, the interaction between the difference frequency component and the second harmonic component is controlled by controlling the frequency and phase of the fundamental wave, whereby a reflected wave component to be imaged is extracted at a high S/N ratio. Incidentally, a method which extracts and images the difference frequency component itself is stated in, for example, Japanese Patent Application No. 2001-110307, but any statement pertaining to the phase control is not contained in the document.

Next, there will be described an imaging method utilizing the difference frequency component in accordance with this embodiment. First, the concept of the imaging method will be elucidated with reference to FIG. 2A-FIG. 8C.

Figure 2B:
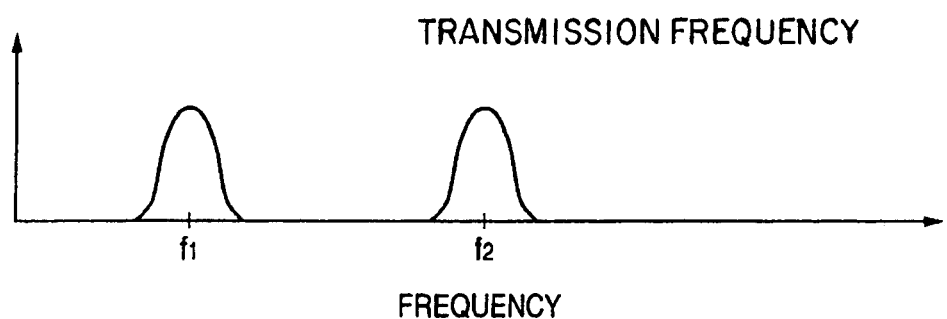
FIGS. 2B and 2C are diagrams for explaining the concept of a method according to this embodiment.
Figure 2C:
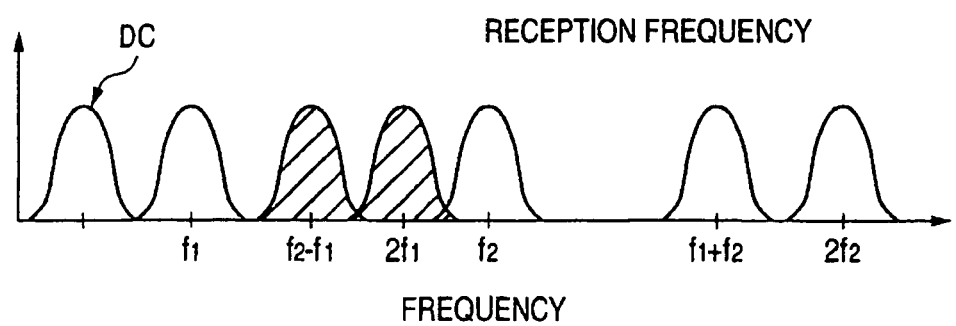

FIG. 2B is a diagram showing the spectrum of ultrasonic waves which have two frequency peaks $f_1$ and $f_2$ (where $f_1 < f_2$) (hereinbelow, the former ultrasonic wave shall be called "first fundamental wave", and the latter ultrasonic wave "second fundamental wave"). FIG. 2C is a diagram showing the spectrum of reflected waves (a reception signal) obtained in a case where a transmission ultrasonic wave constituted by the first fundamental wave and second fundamental wave has been transmitted to a patient. As shown in FIG. 2C, the reception signal contains the reflected waves which correspond to the fundamental wave components of the frequencies $f_1$, $f_2$ constituting the transmission ultrasonic wave, and besides, the difference frequency components (DC, $f_2 - f_1$) and sum frequency components ($2f_1$, $2f_2$, $f_1 + f_2$) of the reflected waves generated by the nonlinearity of in vivo propagation. Here, "DC" denotes a frequency component within a band which is somewhat broad centering round a zero frequency. Further, the sum frequency components of the frequencies $2f_1$, $2f_2$ correspond to the second harmonic wave of the first fundamental wave and that of the second fundamental wave, respectively.

In the method according to this embodiment, note is taken of, for example, the second harmonic component of the first fundamental wave and the difference frequency component of the frequency ($f_2 - f_1$). More specifically, the frequency and phase of the second fundamental wave are controlled so as to superpose the difference frequency component of the frequency ($f_2 - f_1$) on the second harmonic component of the first fundamental wave in inphase fashion. Thus, the component in the vicinity of the second harmonic band of the first fundamental wave is enlarged and imaged, thereby to obtain useful bio-information.

In accordance with this method, the magnitude of the reflected wave component in the vicinity of the second harmonic band of the first fundamental wave can be controlled in the three aspects of a lower frequency side, a higher frequency side and both the sides with respect to the second harmonic band. The respective aspects will be concretely explained below.

Figure 3:
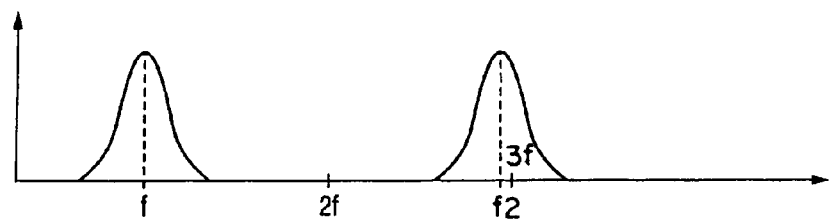
FIG. 3 is a diagram showing the spectrum of a first fundamental wave which has a frequency peak at $f$, and a second fundamental wave which has a frequency peak at $f_2$ ($f<f_2$)
Figure 4A:
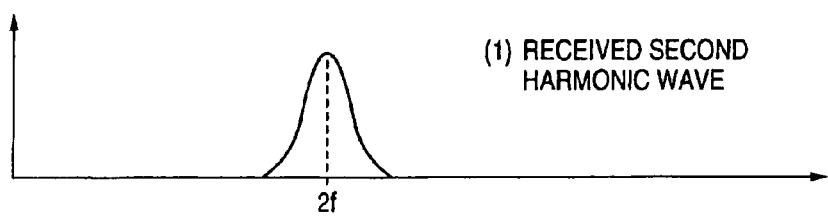
FIGS. 4A, 4B and 4C are diagrams for explaining the interaction between the second harmonic wave of the first fundamental wave and a difference frequency component as based on a method according to the first embodiment.
Figure 4B:
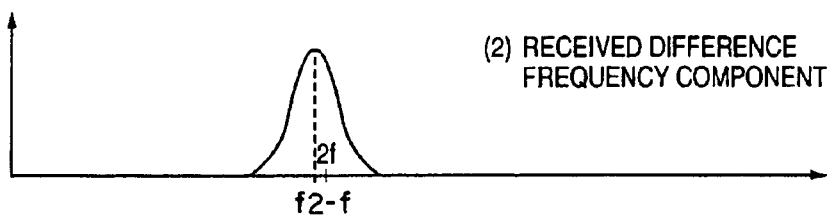
Figure 4C:
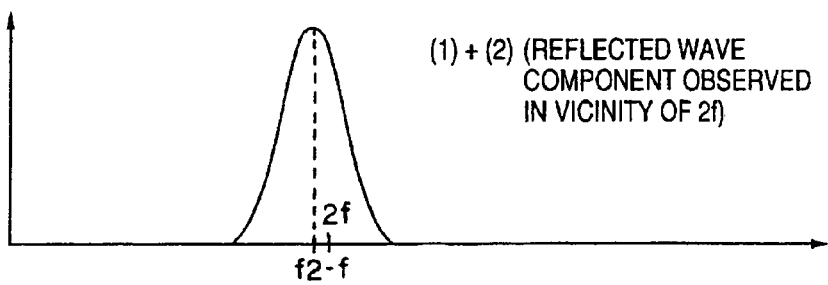

FIG. 3 is a diagram showing the spectrum of a first fundamental wave which has a frequency peak at f, and a second fundamental wave which has a frequency peak at $f_2$ (f<$f_2$). Herein, the frequency peak $f_2$ is assumed to be a value being somewhat smaller than 3f, for example, a value of about 2.8f. In a case where a transmission ultrasonic wave constituted by the fundamental waves having the spectrum has been transmitted to a patient, a reflected wave shown in FIG. 4C, in which the second harmonic wave of the first fundamental wave as shown in FIG. 4A and a difference frequency component (center frequency) shown in FIG. 4B are added up, is measured in the vicinity of a frequency 2f. The reflected wave is equivalent to a wave in which the second harmonic component of the first fundamental wave as has the center frequency of 2f is broadened onto a lower frequency side so as to enlarge its peak.

Figure 5:
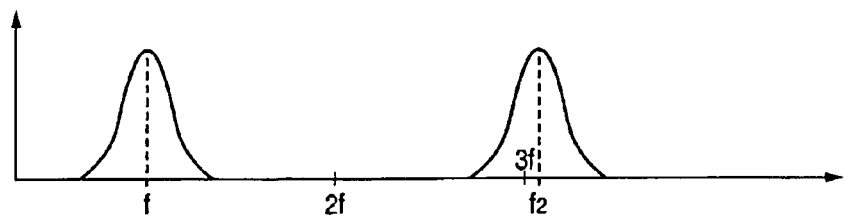
FIG. 5 is a diagram showing the spectrum of a transmission ultrasonic wave which has two frequency peaks $f$ and $f_2$ ($f<f_2$)
Figure 6A:
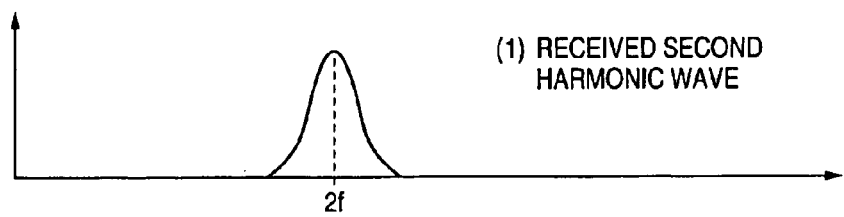
FIGS. 6A, 6B and 6C are diagrams for explaining the interaction between the second harmonic wave of the first fundamental wave and a difference frequency component as based on the method according to the first embodiment.
Figure 6B:
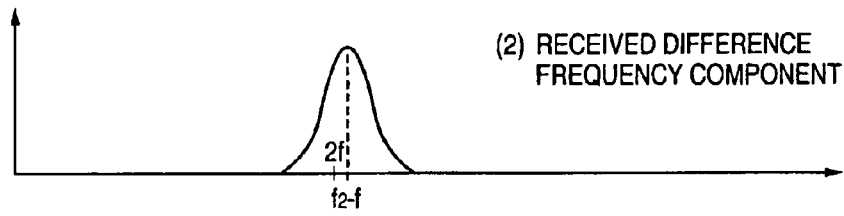
Figure 6C:
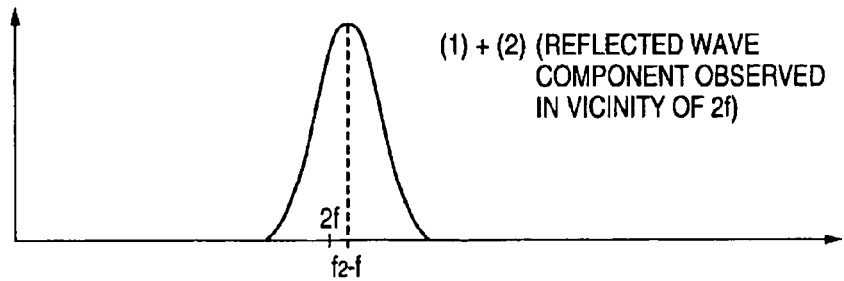

Besides, FIG. 5 is a diagram showing the spectrum of a transmission ultrasonic wave which has, for example, two frequency peaks f and $f_2$ (f<$f_2$). Herein, the frequency peak $f_2$ is assumed to be a value being somewhat larger than 3f, for example, a value of about 3.2f. In a case where ultrasonic waves having the spectrum have been transmitted to a patient, a reflected wave shown in FIG. 6C, in which the second harmonic wave of the first fundamental wave as shown in FIG. 6A and a difference frequency component (center frequency) shown in FIG. 6B are added up, is measured in the vicinity of a frequency 2f. The reflected wave is equivalent to a wave in which the second harmonic wave of the first fundamental wave as has the center frequency of 2f is broadened onto a higher frequency side so as to enlarge its peak.

Figure 7:
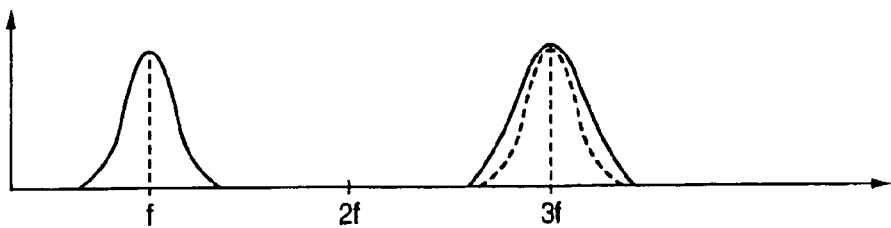
FIG. 7 is a diagram showing the spectrum of a transmission ultrasonic wave which has, for example, two frequency peaks $f$ and $3f$.
Figure 8A:
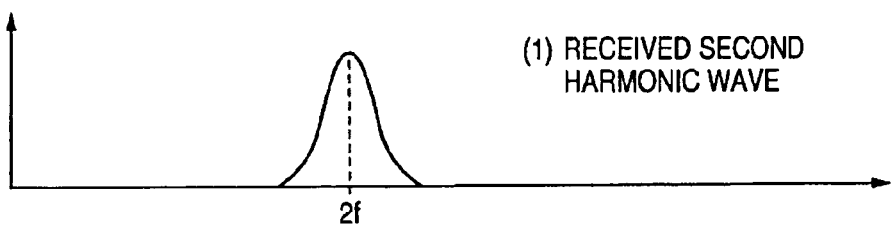
FIGS. 8A, 8B and 8C are diagrams for explaining the interaction between the second harmonic wave of the first fundamental wave and a difference frequency component as based on the method according to the first embodiment.
Figure 8B:
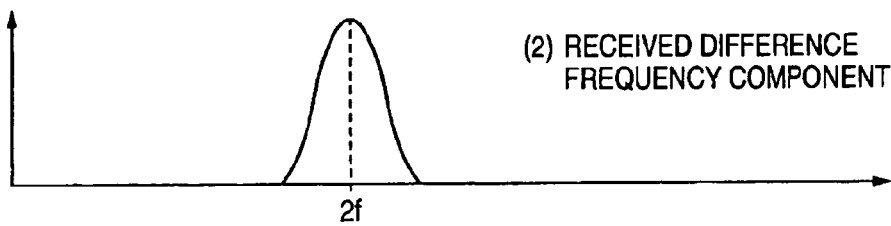
Figure 8C:
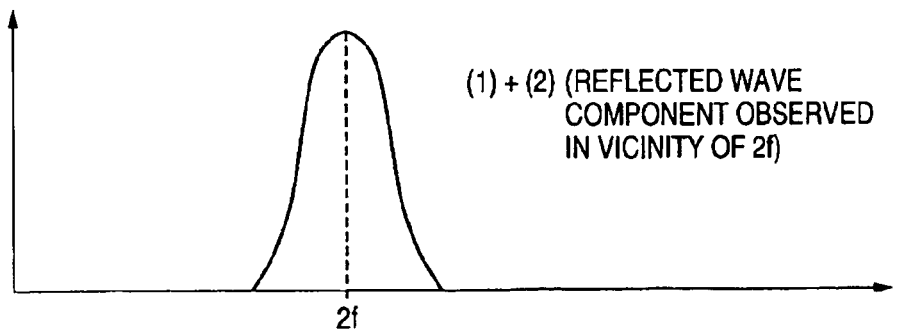

Further, FIG. 7 is a diagram showing the spectrum of a transmission ultrasonic wave which has, for example, two frequency peaks f and 3f. Herein, a fundamental wave which has its peak at 3f is such that the fundamental wave having its peak at f1 in FIG. 3, and the fundamental wave having its peak at f2 in FIG. 5 are added up. In a case where ultrasonic waves having the spectrum have been transmitted to a patient, a reflected wave shown in FIG. 8C, in which the second harmonic wave of the first fundamental wave as shown in FIG. 8A and a difference frequency component (center frequency) shown in FIG. 8B are added up, is measured in the vicinity of a frequency 2f. The reflected wave is equivalent to a wave in which the second harmonic wave of the first fundamental wave has the center frequency of 2f broadened onto a lower frequency side and a higher frequency side so as to enlarge its peak.

Transmission Ultrasonic Wave

Next, there will be explained a transmission ultrasonic wave for causing the difference frequency component to appear. The transmission ultrasonic waves can be classified into the sine type and the cosine type, depending upon whether they are in even symmetry or in odd symmetry with respect to the origin which is set at the center of transmission pulses. Besides, each of the types includes a subtype which generates a difference frequency component that enhances the second harmonic wave of a fundamental wave (that is, a subtype which generates a difference frequency component that has the same polarity as that of the second harmonic wave), and a subtype which generates a difference frequency component that weakens the second harmonic wave (that is, a subtype which generates a difference frequency component that has the opposite polarity to that of the second harmonic wave). Now, the sine type will be explained with reference to FIGS. 9A and 9B, and the cosine type with reference to FIGS. 10A and 10B.

Figure 9A:
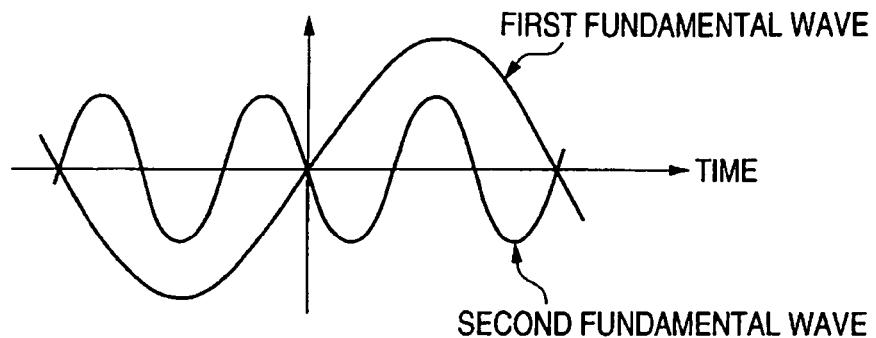
FIGS. 9A and 9B are diagrams for explaining transmission ultrasonic waves of sine type.
Figure 9B:
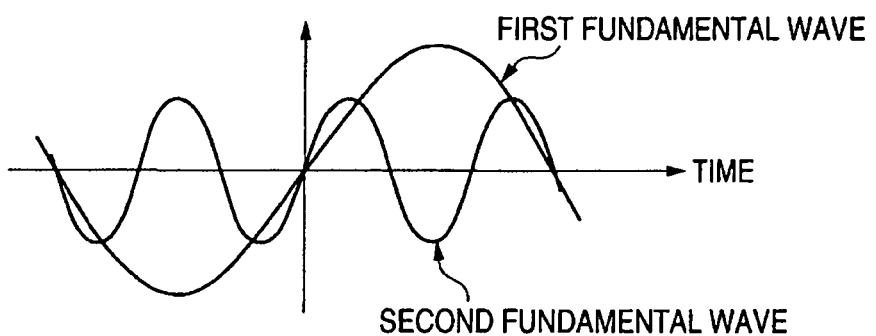

FIG. 9A shows the waveform (central part) of a transmission ultrasonic wave of the sine type for generating the difference frequency component which enhances the second harmonic wave. As shown in the figure, in order to generate the difference frequency component which enhances the second harmonic wave, a second fundamental wave (frequency $f_2$) has its phase controlled so that the crest (trough) of the amplitude of the second fundamental wave may, for example, agree in timing with the crest (trough) of the amplitude of a first fundamental wave (frequency $f_1$). On the other hand, FIG. 9B shows the waveform (central part) of a transmission ultrasonic wave of the sine type for generating the difference frequency component which weakens the second harmonic wave. As shown in the figure, in order to generate the difference frequency component which weakens the second harmonic wave, a second fundamental wave (frequency $f_2$) has its phase controlled so that the crest (trough) of the amplitude of the second fundamental wave may, for example, agree in timing with the trough (crest) of the amplitude of a first fundamental wave (frequency $f_1$).

More specifically, letting the first fundamental wave be $\Psi_1=A_1 \sin(2\pi\omega f_1)$, and the second fundamental wave be $\Psi_2=A_2 \sin(2\pi\omega f_2+\theta)$, a condition for enhancing or weakening the first fundamental wave and the second fundamental wave can be expressed in terms of an initial phase θ (or a phase at the origin defined above), as follows:

Subject to $A_1$, $A_2$>0,
(1) Enhancing condition θ=π
(2) Weakening condition θ=0 or 2π

Figure 10A:
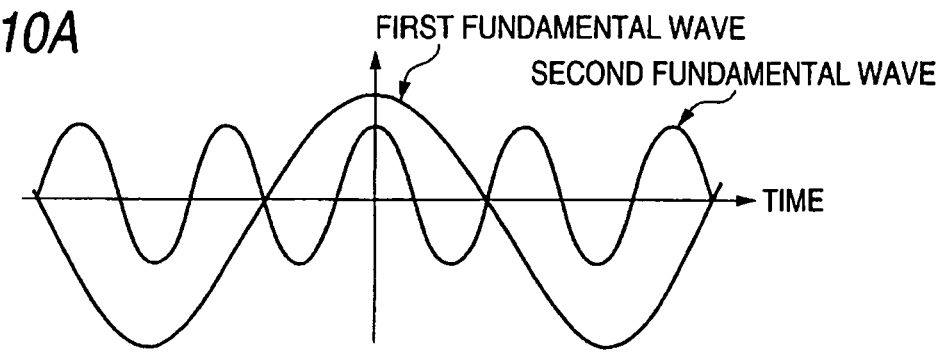
FIGS. 10A and 10B are diagrams for explaining transmission ultrasonic waves of cosine type.
Figure 10B:
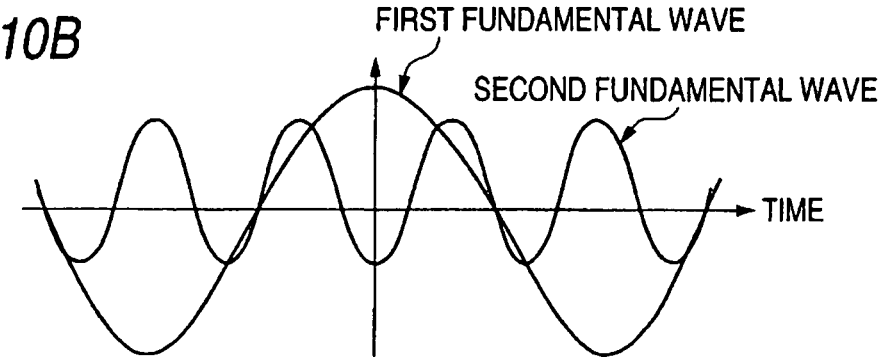

Meanwhile, FIG. 10A shows the waveform (central part) of a transmission ultrasonic wave of the cosine type for generating the difference frequency component which enhances the second harmonic wave. As shown in the figure, in order to generate the difference frequency component which enhances the second harmonic wave, a second fundamental wave (frequency $f_2$) has its phase controlled so that the crest (trough) of the amplitude of the second fundamental wave may, for example, agree in timing with the crest (trough) of the amplitude of a first fundamental wave (frequency $f_1$). On the other hand, FIG. 10B shows the waveform (central part) of a transmission ultrasonic wave of the cosine type for generating the difference frequency component which weakens the second harmonic wave. As shown in the figure, in order to generate the difference frequency component which weakens the second harmonic wave, a second fundamental wave (frequency $f_2$) has its phase controlled so that the crest (trough) of the amplitude of the second fundamental wave may, for example, agree in timing with the trough (crest) of the amplitude of a first fundamental wave (frequency $f_1$).

More specifically, letting the first fundamental wave be $\Psi_1=A_1 \cos(2\pi\omega f_1)$, and the second fundamental wave be $\Psi_2=A_2 \cos(2\pi\omega f_2+\theta)$, a condition for enhancing or weakening the first fundamental wave and the second fundamental wave can be expressed in terms of an initial phase θ, as follows:

Subject to $A_1$, $A_2$>0,
(1) Enhancing condition θ=0 or 2π
(2) Weakening condition θ=π

Incidentally, this embodiment will refer to the case where the second harmonic wave and the difference frequency component enhance each other as will be stated later.

Accordingly, the transmission ultrasonic wave having the waveform shown in FIG. 9A or FIG. 10A (more strictly, ultrasonic wave obtained by superposing the fundamental waves shown in each figure; refer to FIG. 12) is generated by the pulser/amplifier unit 13 under the control of the waveform control unit 14, and it is transmitted from the probe 11. Besides, in the second embodiment which describes the case where the second harmonic wave and the difference frequency component weaken each other as will be stated later, the transmission ultrasonic wave having the waveform shown in FIG. 9B or FIG. 10B (refer to FIG. 17) is generated by the pulser/amplifier unit 13 under the control of the waveform control unit 14, and it is transmitted from the probe 11.

Imaging Method Utilizing Difference Frequency Component

Next, there will be described the operation of the ultrasonic diagnostic equipment 10 in the case of executing an imaging method which utilizes a difference frequency component. This embodiment consists in directly controlling the phase of the second harmonic wave of a fundamental wave, etc., and indirectly controlling the phase of the difference frequency component, thereby to enlarge a harmonic component near the second harmonic band of the first fundamental wave. This embodiment is profitable in case of imaging, for example, a tissue region.

Figure 11:
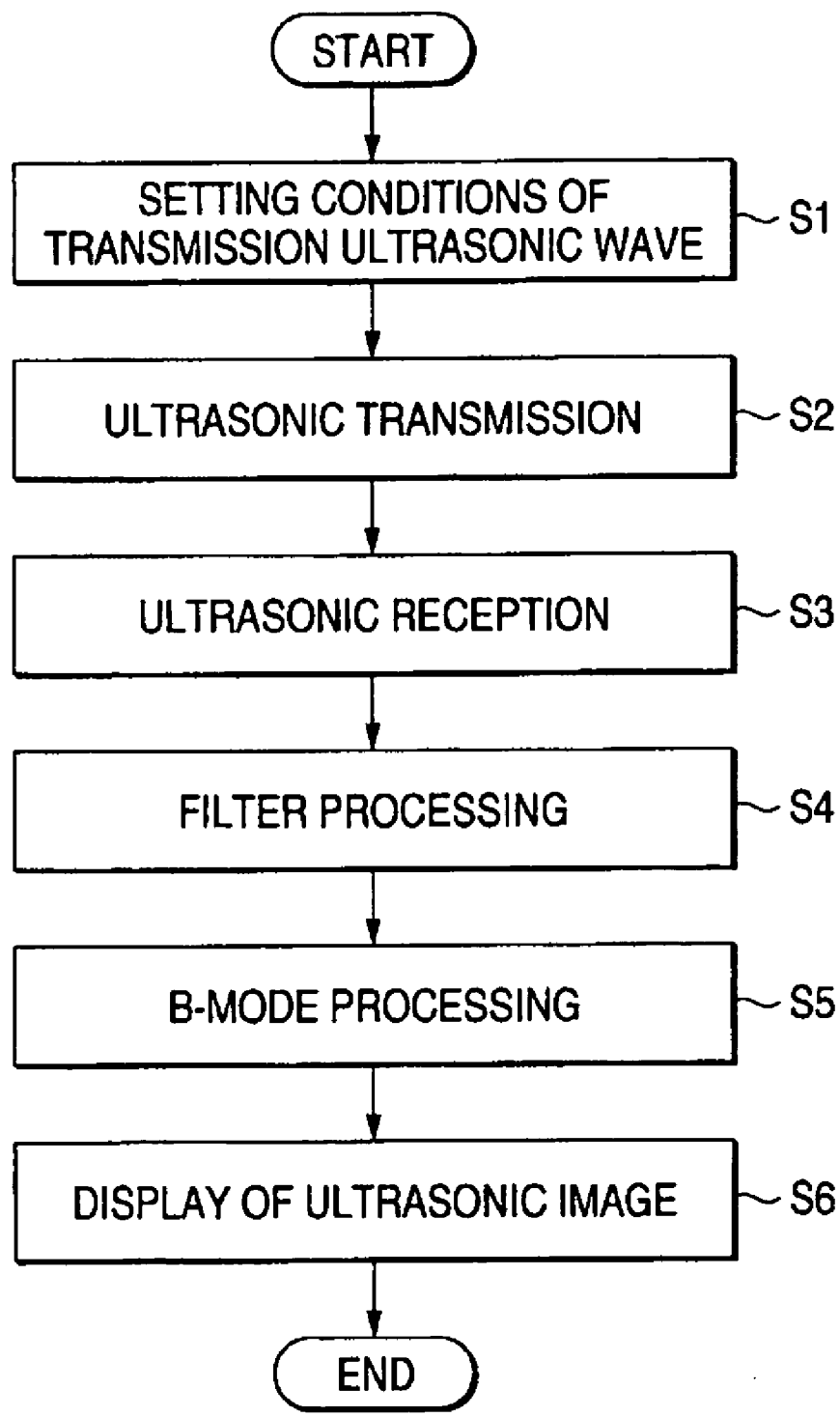
FIG. 11 is a flow chart showing the processing steps of an imaging method utilizing a difference frequency component as is executed by the ultrasonic diagnostic equipment 10.

FIG. 11 is a flow chart showing the processing steps of the imaging method utilizing the difference frequency component as is executed by the ultrasonic diagnostic equipment 10. Referring to the figure, first of all, the conditions of a transmission ultrasonic wave are automatically set (step S1). Here, the "conditions of the transmission ultrasonic wave" signify the frequencies, amplitudes, phases and other physical conditions of first and second fundamental waves for causing the difference frequency component between the second fundamental wave and the first fundamental wave to appear near the frequency of the second harmonic wave of the first fundamental wave. Incidentally, the frequencies being the conditions of the transmission ultrasonic wave may well be preset as the multiple frequencies of a harmonic mode. An operator can select any frequency at will through the input unit 27 from among a plurality of recommended frequencies which are displayed on the display unit 25 for individual purposes.

Concretely, setting as stated below is automatically performed at the step S1. In a case where the difference frequency component is to appear in the vicinity and on the lower frequency side of the frequency of the second harmonic wave of the first fundamental wave (refer to FIG. 3 and FIG. 4), the frequency of the second fundamental wave is set at, for example, 2.8f where f denotes the frequency of the first fundamental wave. On the other hand, in a case where the difference frequency component is to appear in the vicinity and on the higher frequency side of the frequency of the second harmonic wave of the first fundamental wave (refer to FIG. 5 and FIG. 6), the frequency of the second fundamental wave is set at, for example, 3.2f where f denotes the frequency of the first fundamental wave. Besides, in a case where the difference frequency component is to appear in the vicinity and on the lower and higher frequency sides of the frequency of the second harmonic wave of the first fundamental wave (refer to FIG. 7 and FIG. 8), the frequency of the second fundamental wave is set at, for example, 3f where f denotes the frequency of the first fundamental wave. Further, the polarities and amplitudes of the first and second fundamental waves are controlled so as to enhance the second harmonic wave and the difference frequency component each other.

Figure 12A:
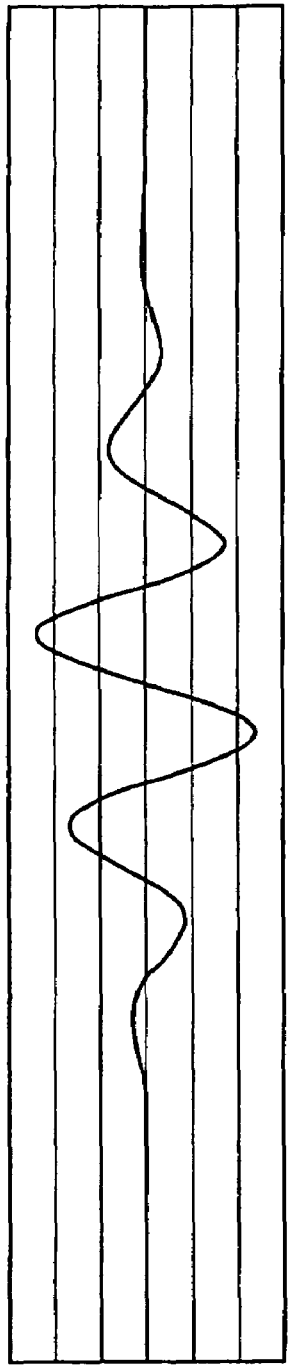
FIGS. 12A and 12B are diagrams for explaining an ultrasonic wave which is transmitted in the first embodiment.

FIG. 12A shows examples of the ultrasonic pulses of the respective fundamental waves in the case of n=6 (where n denotes a wave number). A burst wave concerning the first fundamental wave and a burst wave concerning the second fundamental wave as shown in the figure are added up, whereby a transmission ultrasonic wave shown in FIG. 12B is generated.

Incidentally, apart from the automatic setting stated above, the setting of the conditions of the fundamental waves at the step S1 may well be so schemed that the operator manually sets the conditions on the basis of, for example, patient information, diagnostic information containing an imaging part, and the selection of an imaging mode.

Figure 12B:
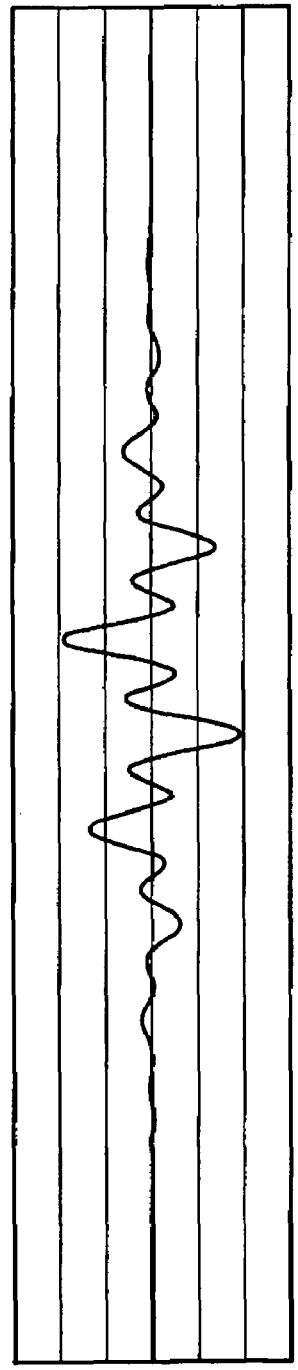

Subsequently, a transmission ultrasonic wave shown in FIG. 12B is transmitted into a patient (step S2), and the resulting reflected wave is received as an echo signal (step S3). The echo signal has a peak constituted by the second harmonic wave of the first fundamental wave and the difference frequency component, in the vicinity of a frequency band of 2f.

After undergoing processing such as amplification and delay addition, the echo signal is subjected to filtering by the filter processing unit 18 (step S4). By way of example, the filtering proceeds in such a manner that the echo signal is passed through a band centering at a frequency of 2f (a band in which a tissue harmonic echo component is predominant), and that bands before and behind the above band are all attenuated.

Subsequently, the filtered echo signal is subjected to predetermined processing in the B-mode processing unit 19 (or the Doppler processing unit 21) (step S5), and the resulting signal is displayed as an ultrasonic image on the display unit 25 (step S6).

In accordance with the configuration stated above, advantages to be stated below can be attained.

In accordance with the method according to this embodiment, the phase of the difference frequency component between the fundamental waves constituting the transmission ultrasonic wave, etc. are controlled, whereby the difference frequency component and the second harmonic component can interact so as to enhance each other. Thus, the second harmonic component can be enlarged on its lower frequency side or/and higher frequency side, and the reflected wave component to-be-imaged can be enhanced. As a result, the method can heighten the versatility of band design as compared with the prior-art second harmonic imaging. Moreover, an imaging signal can be extracted at a high S/N ratio, and useful bio-information can be offered at medical sites.

Besides, in accordance with the ultrasonic diagnostic equipment according to this embodiment, the phase of the difference frequency component between the fundamental waves constituting the transmission ultrasonic wave, etc. can be set, not only manually, but also automatically with the diagnostic information etc. Moreover, since the recommended combinations of the individual fundamental wave frequencies are displayed for the respective purposes, the setting of the frequencies for the interaction between the difference frequency component and the second harmonic component can be performed easily and quickly.

Second Embodiment

Now, the second embodiment of the present invention will be described. The second embodiment consists in controlling the phase of a difference frequency component so as to remove or reduce the second harmonic component of a first fundamental wave. This example is profitable in a case, for example, where, as disclosed in Japanese Patent Application No. 2001-343577, in the contrast echo, a tissue image and a contrast medium echo are separated in a band which is about 1.5 times the frequency of the first fundamental wave, so as to image the contrast medium echo.

The general concept of an imaging method utilizing a difference frequency component will be described with reference to FIGS. 13 and 14.

Figure 13:
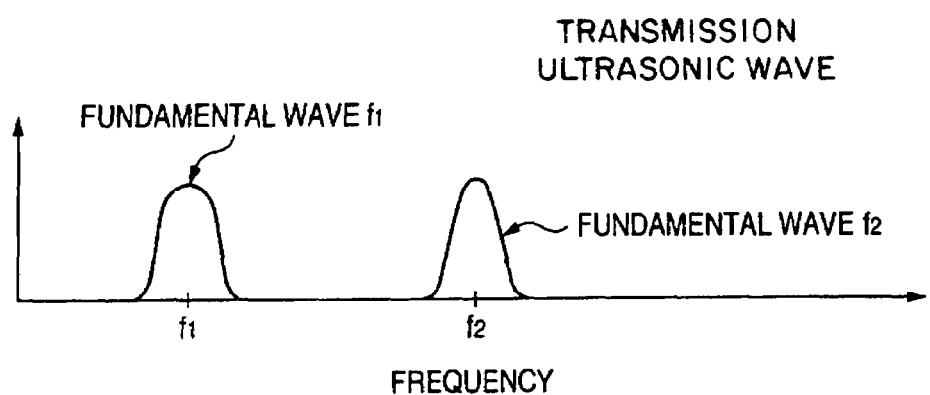
FIG. 13 is a diagram showing the spectrum of a transmission ultrasonic wave which is generated by adding up a first fundamental wave having a frequency peak $f_1$, and a second fundamental wave having a frequency peak $f_2$ ($f_1<f_2$)

FIG. 13 is a diagram showing the spectrum of a transmission ultrasonic wave which is generated by adding up a first fundamental wave having a frequency peak $f_1$, and a second fundamental wave having a frequency peak $f_2$ ($F_1 < f_2$). Incidentally, the first fundamental wave and second fundamental wave have the weakening relationship shown in, for example, FIG. 9B or FIG. 10B.

Figure 14:
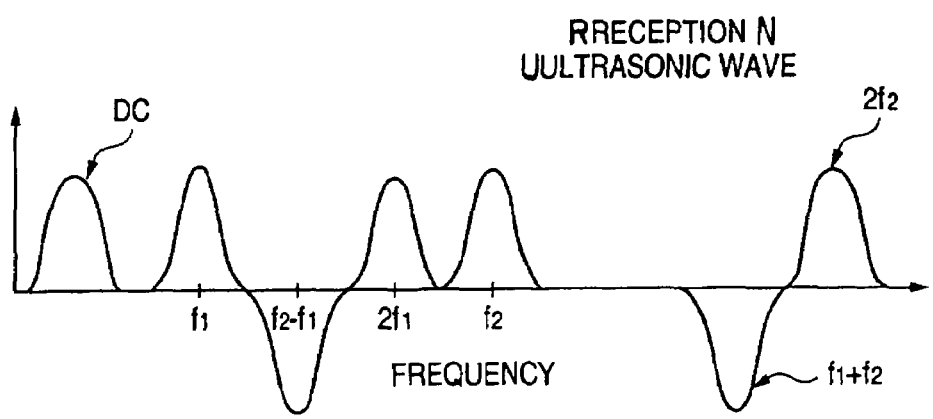
FIG. 14 is a diagram showing the spectrum of reflected wave components which are obtained in a case where the ultrasonic wave constituted by the first and second fundamental waves as shown in FIG. 13 has been transmitted to a patient.

Besides, FIG. 14 is a diagram showing the spectrum of reflected wave components which are obtained in a case where the ultrasonic wave constituted by the first and second fundamental waves as shown in FIG. 13 has been transmitted to a patient. As shown in FIG. 14, the reflected wave components contain reflected waves which correspond to the fundamental wave components of the frequencies $f_1$, $f_2$ constituting the transmission ultrasonic wave, and besides, the difference frequency components (DC, $f_2-f_1$) and sum frequency components ($2f_1$, $2f_2$, $f_1+f_2$) of reflected waves generated by the nonlinearity of in vivo propagation. Here, the sum frequency components of the frequencies $2f_1$, $2f_2$ correspond to the second harmonic wave of the first fundamental wave and that of the second fundamental wave, respectively.

In the second embodiment, the transmission frequency $f_2$ is controlled so as to equalize the frequencies ($f_2-f_1$) and $2f_1$, whereby the second harmonic component of the first fundamental wave is cancelled by the difference frequency component of the frequency ($f_2-f_1$). Thus, in the contrast echo by way of example, the tissue harmonic component in the vicinity of a $2f_1$ band can be removed, and the reflected wave component from a contrast medium can be extracted at a high accuracy.

Figure 15:
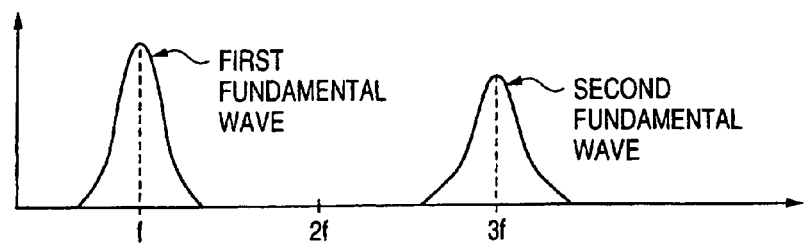
FIG. 15 is a diagram showing the spectrum of a first fundamental wave which has a frequency peak at $f$, and a second fundamental wave which has a frequency peak at $3f$.
Figure 16A:
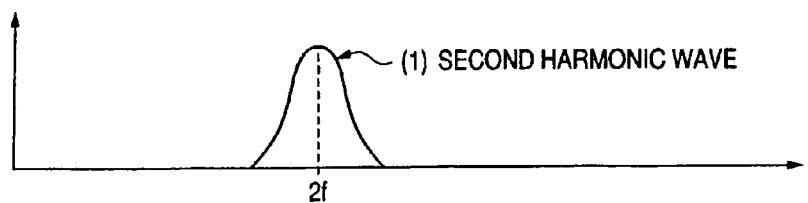
FIGS. 16A, 16B and 16C are diagrams for explaining the interaction between the second harmonic wave of the first fundamental wave and a difference frequency component as is based on a method according to a second embodiment.
Figure 16B:
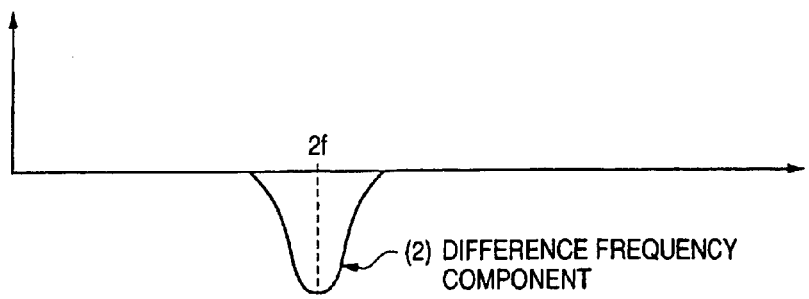
Figure 16C:
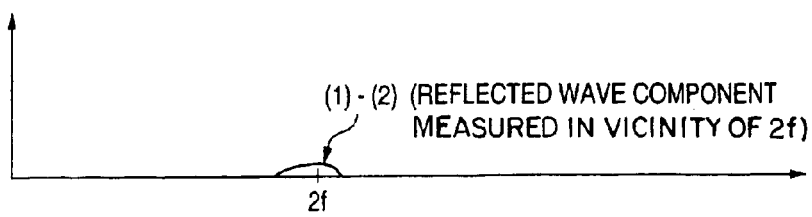

FIG. 15 is a diagram showing the spectrum of a first fundamental wave which has a frequency peak at f, and a second fundamental wave which has a frequency peak at 3f. In a case where a transmission ultrasonic wave constituted by the fundamental waves having the spectrum has been transmitted to a patient, a reflected wave shown in FIG. 16C, in which the second harmonic wave of the first fundamental wave as shown in FIG. 16A and a difference frequency component (center frequency) shown in FIG. 16B are added up, is measured in the vicinity of a frequency 2f. Incidentally, the second harmonic wave of the first fundamental wave is ideally cancelled by the difference frequency component (becomes zero).

Next, the operation of the ultrasonic diagnostic equipment 10 in the case of executing an imaging method which utilizes a difference frequency component will be described with reference to FIG. 11.

First, the conditions of a transmission ultrasonic wave are set through the input unit 27 or automatically (step S1).

Figure 17A:
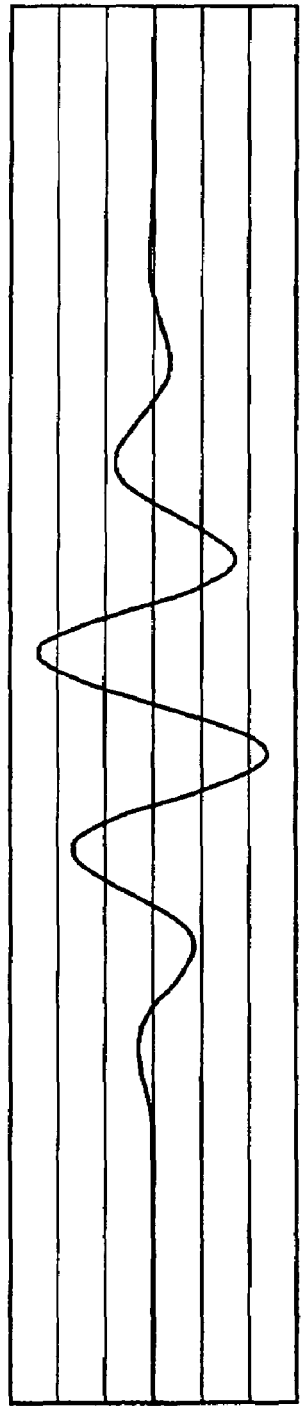
FIGS. 17A and 17B are diagrams for explaining an ultrasonic wave which is transmitted in the second embodiment.
Figure 17B:
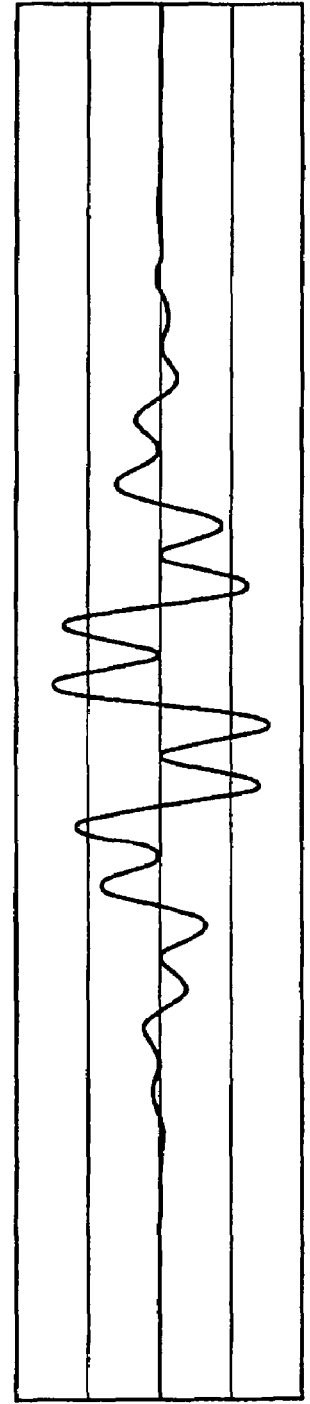

FIG. 17A shows examples of the ultrasonic pulses of the respective fundamental waves in the case of n=6. A first burst wave concerning the first fundamental wave and a second burst wave concerning the second fundamental wave (however, phases are inverted to those in the case of FIG. 12B) as shown in the figure are added up, whereby the transmission ultrasonic wave shown in FIG. 17B is generated.

Incidentally, the setting of the conditions of the transmission ultrasonic wave at this step may be realized by the automatic setting or selection setting stated in the first embodiment.

Then, substantially the same processing as in the first embodiment is performed, whereby a reflected wave component with a second harmonic component cancelled by a difference frequency component can be extracted at a high accuracy. The extracted contrast medium echo is imaged, whereby useful bio-information can be obtained quickly and easily.

Third Embodiment

Next, the third embodiment will be described. This embodiment consists in that the sum frequency component between a first fundamental wave and a second fundamental wave is caused to interact with the second harmonic wave of the first fundamental wave or second fundamental wave, thereby to realize imaging in a wide band, imaging at a high S/N ratio, etc. Now, the interaction in which the sum frequency component and the second harmonic wave are superposed and intensified each other will be explained with reference to FIGS. 18-20 by way of example.

Figure 18A:
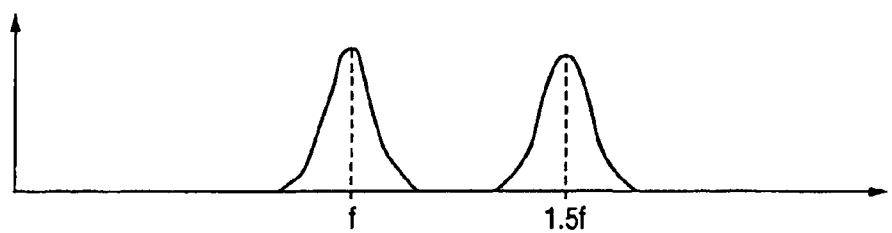
FIG. 18A is a diagram showing the spectrum of a first fundamental wave which has a frequency peak at $f$, and a second fundamental wave which has a frequency peak at $1.5f$.

FIG. 18A is a diagram showing the spectrum of a first fundamental wave which has a frequency peak at f, and a second fundamental wave which has a frequency peak at 1.5f. In a case where a transmission ultrasonic wave constituted by the fundamental waves having the spectrum has been transmitted to a patient, there are generated the second harmonic waves of the first and second fundamental waves as have a spectrum shown in FIG. 18B, and a difference frequency component and a sum frequency component having a spectrum shown in FIG. 18C. Accordingly, when reflected waves in which the second harmonic waves and the difference and sum frequency components are composited are received, the spectrum thereof comes to have a wide band as shown in FIG. 18D by way of example.

Figure 18B:
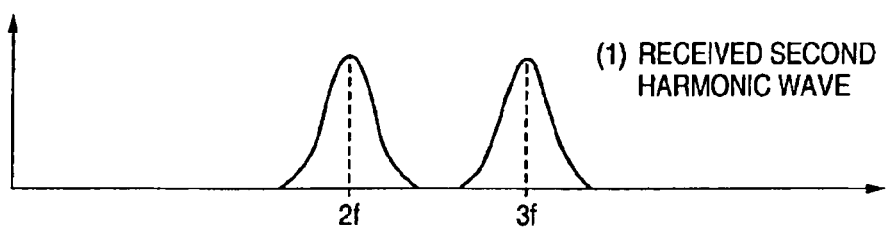
FIG. 18B is a diagram showing the spectrum of the second harmonic waves of the first fundamental wave and second fundamental wave shown in FIG. 18A.
Figure 18C:
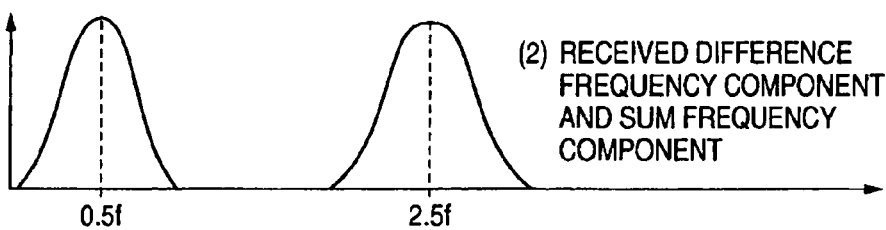
FIG. 18C is a diagram showing the spectrum of the difference frequency component and sum frequency component between the first fundamental wave and second fundamental wave shown in FIG. 18A.
Figure 18D:
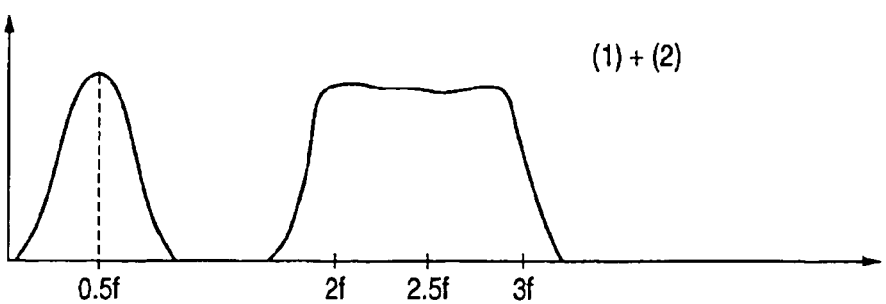
FIG. 18D is a diagram showing the spectrum of reflected waves in which the second harmonic waves shown in FIG. 18B, and the difference frequency component and sum frequency component shown in FIG. 18C are composited.
Figure 19A:
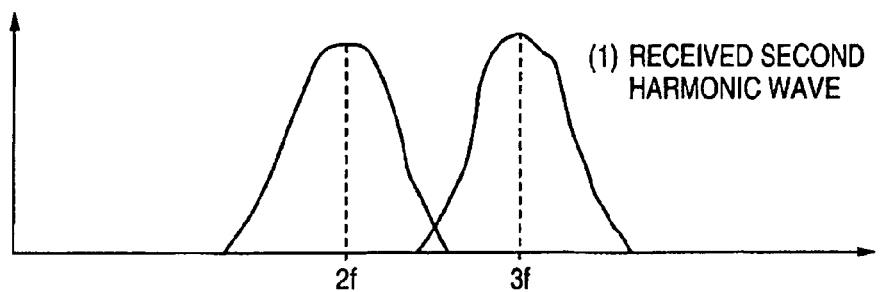
FIG. 19A is a diagram showing the spectrum of the second harmonic waves of the first fundamental wave and second fundamental wave shown in FIG. 18A.
Figure 19B:
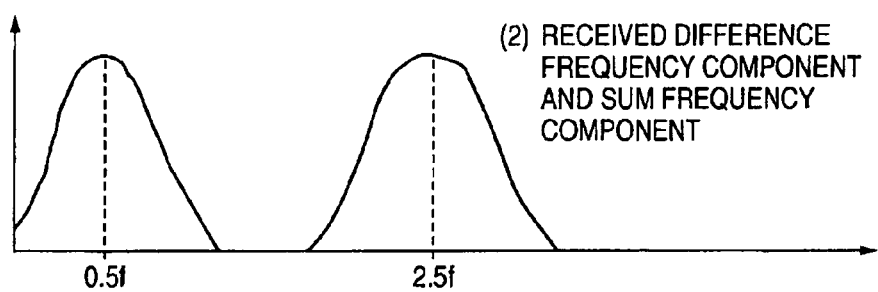
FIG. 19B is a diagram showing the spectrum of the difference frequency component and sum frequency component between the first fundamental wave and second fundamental wave shown in FIG. 18A.
Figure 19C:
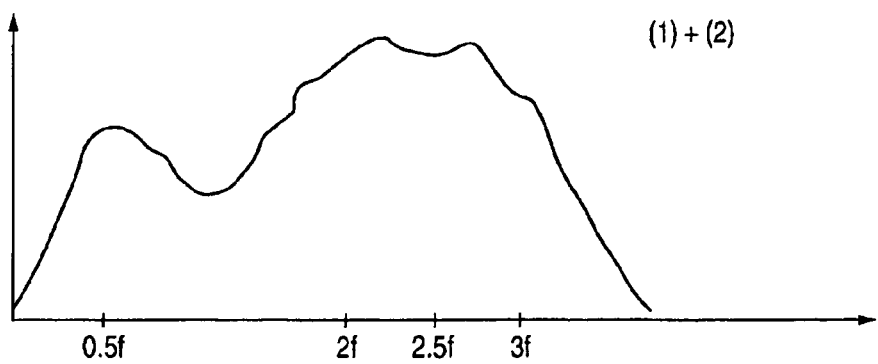
FIG. 19C is a diagram showing the spectrum of reflected waves in which the second harmonic waves shown in FIG. 19A, and the difference frequency component and sum frequency component shown in FIG. 19B are composited.

Besides, as shown in FIGS. 19A and 19B, the second harmonic waves, difference frequency component and sum frequency component which are obtained by the ultrasonic transmission appear in bands wider than in FIGS. 18B and 18C, in some cases. In such a case, when the reflected waves in which they are composited are received, the spectrum of the harmonic components with the fundamental waves excluded comes to have a wide band in which the difference frequency component is also superposed as shown in FIG. 19C by way of example.

Next, the operation of the ultrasonic diagnostic equipment 10 in the case of executing an imaging method which utilizes the sum frequency component will be described with reference to FIG. 11. This embodiment consists in directly controlling the frequency of the first fundamental wave and the phase and frequency of the second fundamental wave, and indirectly controlling the frequency and phase of the sum frequency component, thereby to widen the band of the reflected waves. This embodiment is profitable in a case, for example, where harmonic components derived by phase inversion are subjected to frequency compounding and are then imaged. Here, the "frequency compounding" signifies that a received signal is divided into a plurality of frequency bands, that the signals of the respective bands are subjected to filter processing and B-mode processing, and that the processed results are composited (added).

Referring to FIG. 11, first of all, the conditions of a transmission ultrasonic wave are automatically set (step S1). Here, the "conditions of the transmission ultrasonic wave" signify the frequencies, amplitudes, phases and other physical conditions of first and second fundamental waves for causing the sum frequency component between the second fundamental wave and the first fundamental wave to appear in the vicinity of the higher frequency side of the second harmonic wave of the first fundamental wave. Incidentally, the frequencies being the conditions of the transmission ultrasonic wave are preset as the multiple frequencies of a harmonic mode, as in the case of the difference frequency component.

Concretely, setting as stated below is automatically performed at the step S1. In order to superpose the sum frequency component on the second harmonic waves of the first fundamental wave and second fundamental wave, the center frequency of the first fundamental wave is set at, for example, $f_1$=1.6 MHz, and that of the second fundamental wave is set at, for example, $f_2$=2.5 MHz. Besides, the polarities and amplitudes of the first and second fundamental waves are controlled so as to enhance the second harmonic waves and the sum frequency component each other.

Subsequently, the transmission ultrasonic wave is transmitted into a patient (step S2), and the resulting reflected waves are received as an echo signal (step S3).

Figure 20A:
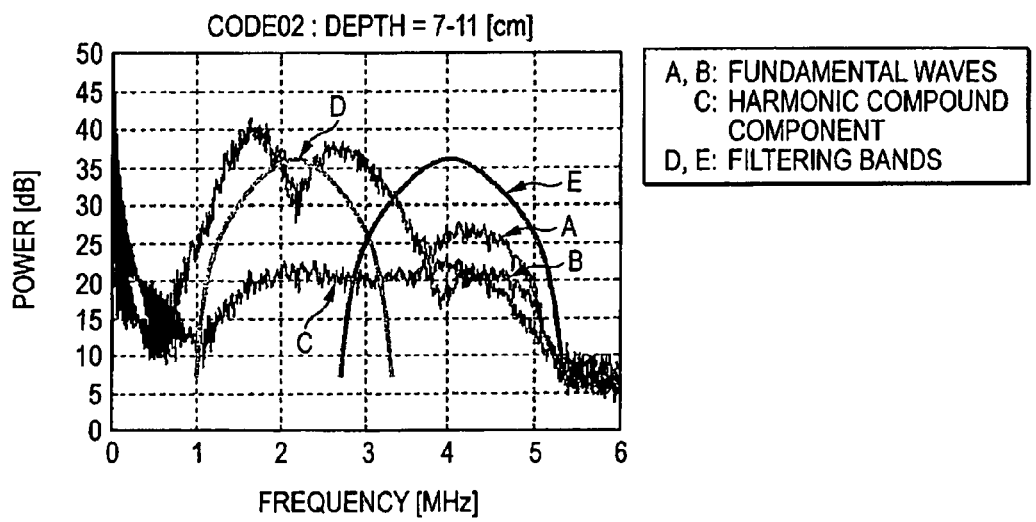
FIG. 20A is a graph showing the spectrum of an echo signal based on a method according to a third embodiment.

FIG. 20A is a graph showing the spectrum of the echo signal obtained in such a way that the transmission ultrasonic wave constituted by the above fundamental waves has its polarity inverted and is then transmitted at 2 rates (pulse inversion transmission). As shown in the figure, owing to the interaction between the sum frequency component and the second harmonic waves, the spectrum C of harmonics (in which the difference frequency component, the second harmonic wave of the first fundamental wave, and the sum frequency component are superposed, and which shall be called "harmonic component" below) in the echo signal can be caused to appear in a wide band. Accordingly, bands D and E for use in the frequency compounding can be set wide.

Figure 20B:
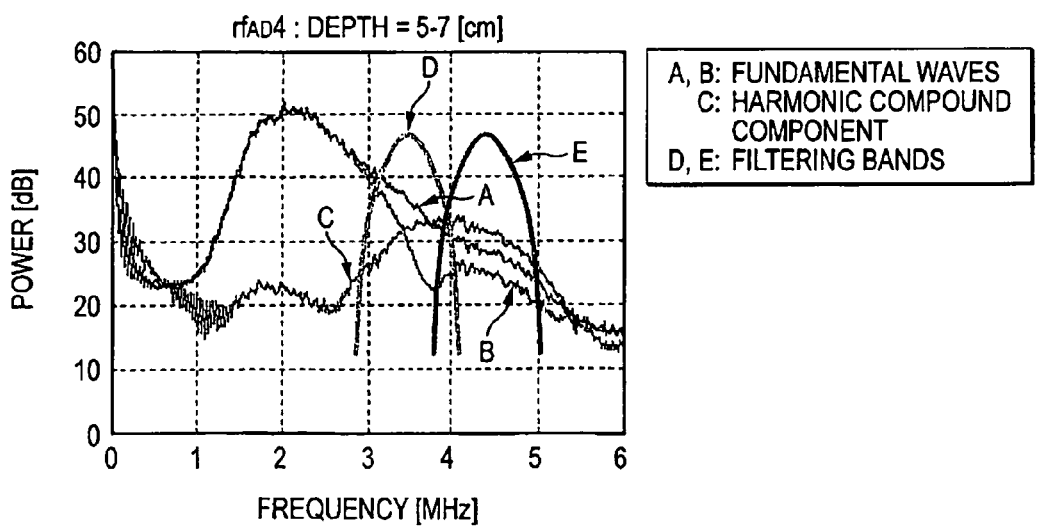
FIG. 20B shows the comparative example of the method in FIG. 20A.

On the other hand, FIG. 20B is a graph showing the spectrum of an echo signal obtained in such a way that an ultrasonic wave having a center frequency f=2.1 MHz in the figure has its polarity inverted and is then transmitted at 2 rates (pulse inversion transmission). In the ultrasonic transmission, a sum frequency component and second harmonic components do not interact. As seen from the figure, a harmonic component C in an echo signal appears in a band width which is narrower than in the case of FIG. 20A where the sum frequency component and the second harmonic waves interact. Accordingly, a distance resolution is not satisfactory, and a speckle reducibility is not high, either.

After the respective bands of the obtained harmonic component as indicated at D and E in FIG. 20A have undergone such processing as amplification and delay addition, they are subjected to filtering by the filter processing unit 18 (step S4). The filtering can be performed in comparatively wide bands as shown in FIG. 20A by way of example.

Subsequently, the individual filtered echo signals undergo predetermined processing in the B-mode processing unit 19 (or the Doppler processing unit 21) (step S5), and they are thereafter composited so as to be displayed as an ultrasonic image on the display unit 25 (step S6).

In accordance with the method according to this embodiment, the frequency, phase etc. of the first fundamental wave or second fundamental wave are controlled, whereby the sum frequency component and the second harmonic component can interact so as to enhance each other. Thus, the second harmonic wave of the first fundamental wave can be enlarged on its higher frequency side, and the second harmonic wave of the second fundamental wave on its lower frequency side, so that the reflected wave component to-be-imaged is enhanced. As a result, a distance resolution can be enhanced. Moreover, since the difference between the frequencies to be compounded is large, a highly effective speckle reducibility can be realized.

Incidentally, this embodiment has been described by exemplifying the interaction in which the sum frequency component and the second harmonic wave are superposed and intensified each other. In contrast, it is also possible to give rise to an interaction in which the sum frequency component and the second harmonic wave are cancelled each other. For this purpose, the phase of at least one of the first and second fundamental waves may be controlled so as to endow the fundamental waves with the weakening relationship as shown in FIG. 9B or FIG. 10B, by way of example.

Fourth Embodiment

Figure 1B:
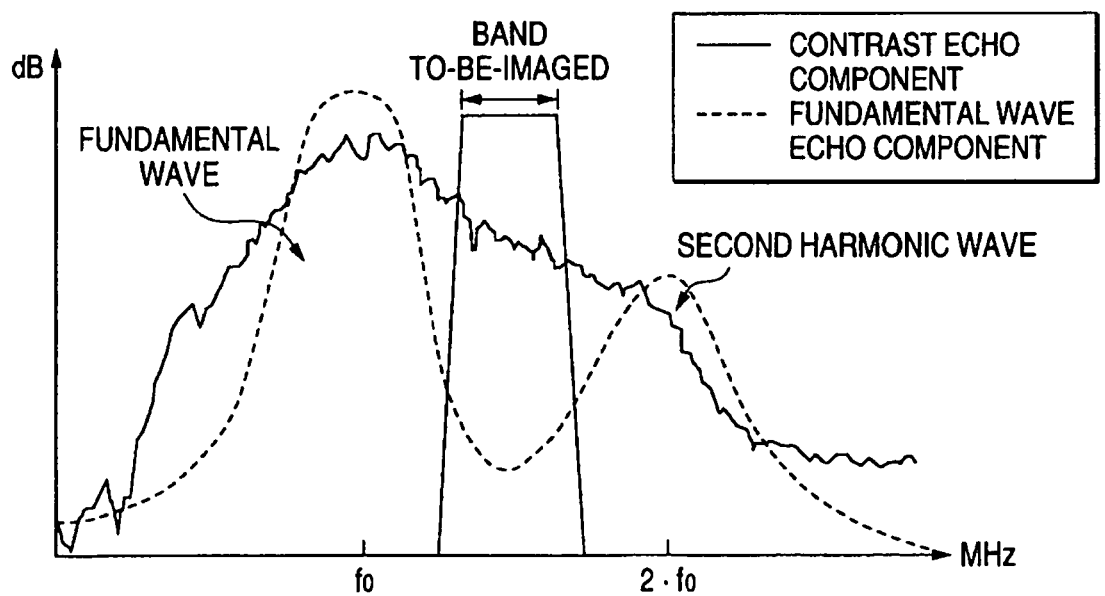
FIG. 1B is a diagram for explaining the prior art.

Next, the fourth embodiment of the present invention will be described. The fourth embodiment consists in that the phase control of the difference frequency component as explained in the first embodiment, or the phase control of the sum frequency component as explained in the third embodiment is executed in a Doppler mode. Now, the phase control of the difference frequency component as explained in the first embodiment (that is, the case where the difference frequency component and the second harmonic wave enhance each other) will be taken as an example and described with reference to FIG. 1.

In general, in the Doppler mode, a plurality of times of ultrasonic receptions are performed for a single scanning line. In each of transmissions for the single scanning line, the waveform control unit 14 transmits an ultrasonic wave which generates a difference frequency component that enhances a second harmonic wave. As already stated, the transmission ultrasonic wave is generated by superposing a first fundamental wave and a second fundamental wave the crests (or troughs) of which are inphase to each other.

When a reception echo signal corresponding to each transmission ultrasonic wave has been received, the signal processing unit 17 extracts the signal component of a second harmonic band (that is, a signal component in which the difference frequency component is superposed on the second harmonic wave) from the reception echo signal.

The Doppler processing unit 21 extracts contrast medium echo components based on the Doppler effect, on the basis of such extracted signal components of the second harmonic bands, and it finds a mean speed, variance, power, and the like information at multiple points. The information items are sent to the DSC 23, and are color-displayed on the display unit 25 as a mean speed image, a variance image, a power image, and a Doppler image in which they are combined.

Thus far, there has been exemplified the case where, in the Doppler mode, the difference frequency component and the second harmonic wave interact so as to enhance each other. In contrast, in a case where a difference frequency component and a second harmonic wave interact so as to weaken each other, an ultrasonic wave which generates the difference frequency component that weakens the second harmonic wave is transmitted in each of a plurality of times of ultrasonic transmissions for a single scanning line. As already stated, the transmission ultrasonic wave is set by superposing a first fundamental wave and a second fundamental wave the crest of one of which and the trough of the other of which are inphase.

In accordance with the above configuration, even in the Doppler mode, the same advantages as in the first embodiment can be attained. This embodiment is especially profitable in the imaging of, for example, the coronary arteries.

Fifth Embodiment

Next, the fifth embodiment of the present invention will be described. This embodiment consists in that the phase, amplitude and polarity of a difference frequency component or a sum frequency component are controlled, thereby to cancel the leakage of a fundamental wave by the difference frequency component. The leakage of the fundamental wave is ascribable to characteristics inherent in the ultrasonic diagnostic equipment 10. Now, a case of utilizing the difference frequency component will be taken as an example and described.

In general, each electric or electronic circuit for use in the equipment should preferably be such that the input and output thereof are linear, from the viewpoints of control etc. However, each circuit does not have a linear input-output relationship in a strict sense, but it involves a nonlinearity. Especially in case of using a digital circuit, the nonlinearity of the circuit is induced by compositing in the conversion of a digital signal into an analog signal, etc.

Figure 21:
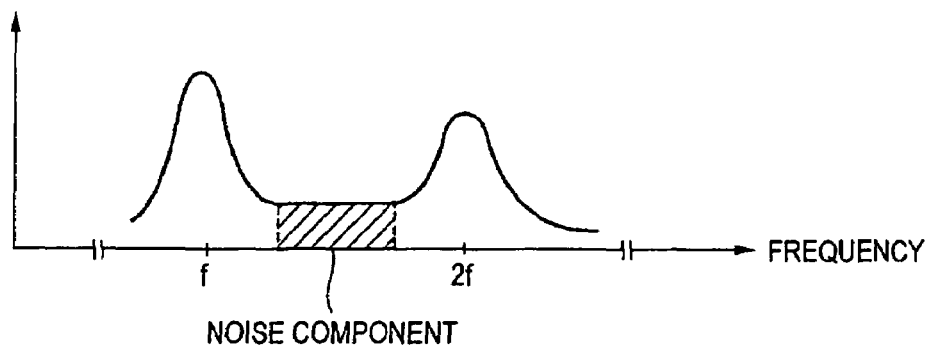
FIG. 21 is a diagram showing noise which is ascribable to the nonlinearity of a circuit.

Also in the ultrasonic diagnostic equipment 10, the leakage of a fundamental wave as shown in FIG. 21 is sometimes induced for the reason that a reception signal is influenced by the nonlinearity of, for example, a digital wave former used in the transmission/reception circuit 15 or a circuit used in any other constituent.

With the method according to this embodiment, the leakage of the fundamental wave attributed to the nonlinearity of the circuit and precision limitation is removed or reduced by the difference frequency component. By way of example, in case of removing a noise component shown in FIG. 21, an ultrasonic wave constituted by a first fundamental wave whose frequency peak lies at $f$, and a second fundamental wave whose frequency peak lies at 2.5f, is transmitted at ultrasonic transmission so that the difference frequency component may appear near 1.5f. On this occasion, the amplitude of the second fundamental wave is so that the difference frequency component between the first and second fundamental waves may become substantially equal to the noise component ascribable to the nonlinearity of the circuit, and the polarity of the second fundamental wave is set so as to become inverse to the polarity of the first fundamental wave (refer to the first embodiment).

Owing to such a configuration, the difference frequency component can be caused to appear as a corresponding spectrum in a band in which the noise component ascribable to the nonlinearity of the circuit is to be removed. In the reception signal, accordingly, the noise component and the difference frequency component are cancelled from each other, and the noise component can be removed or reduced.

Sixth Embodiment

Next, the sixth embodiment will be described. This embodiment consists in applying the technological idea of the present invention to a case where a plurality of times of ultrasonic transmissions/receptions are performed in the contrast echo, and where a contrast medium echo is extracted by a subtraction method for the purpose of deleting a motion artifact. Now, a case of utilizing a difference frequency component will be taken as an example and described.

In general, a reflected wave to be received is influenced by the motion of a patient. The motion appears as a motion artifact on an image in, for example, an imaging method which employs a plurality of times of ultrasonic transmissions/receptions. In this embodiment, the phase of the difference frequency component, etc. are controlled, thereby to remove or reduce the leakage component of a fundamental wave as arises in each reception ultrasonic wave, and the difference of echo signals is taken between different rates, thereby to remove or reduce the motion artifact and the like noise component which arise.

More specifically, first of all, a transmission ultrasonic wave which is generated by adding up a first fundamental wave having a frequency peak $f_1$ and a second fundamental wave having a frequency peak $f_2$ ($f_1<f_2$), is transmitted at, at least, 2 rates at predetermined timings. The transmission ultrasonic wave is generated so that the phases of the second harmonic wave and the difference frequency component may be reversed. Besides, in the ensuing description, the transmission ultrasonic wave shall be transmitted at 2 rates.

When an echo signal corresponding to each transmission ultrasonic wave is received, it is subjected to predetermined processing such as amplification and A/D conversion. To be noted here is that, in each echo signal, the leakage component of the fundamental wave has been removed or reduced by the difference frequency component.

The received echo signals undergo the predetermined processing such as amplification and A/D conversion, and they are subjected to subtraction between the different rates by the signal processing unit 17, whereby a contrast medium echo signal is extracted. This operation is based on a principle stated below.

In the reception signal obtained at each rate, components which are other than a contrast medium echo component originate from tissues. On the other hand, the contrast medium echo component originates from a contrast medium in the body fluid. Since the contrast medium undergoes changes (such as rupture) by the transmission ultrasonic wave, the temporal signal transition of the contrast medium echo component between the rates is considered to be larger as compared with that of the components originating from the tissues. Accordingly, when the reception signal of the first rate is subtracted from that of the second rate by way of example, the components originating from the tissues consist only of a component originating from the motion, and the contrast medium echo component having a higher spectrum is relatively enhanced. Effective blood flow information can be imaged by imaging the enhanced component.

In this embodiment, the reduction of the motion artifact in an image can be realized by the subtraction processing. Now, a case where the motion artifact appears at a rate of, for example, 10% of a signal originating from the tissues in an imaging band will be taken as an example and described with reference to FIGS. 22 and 23.

Figure 22A:
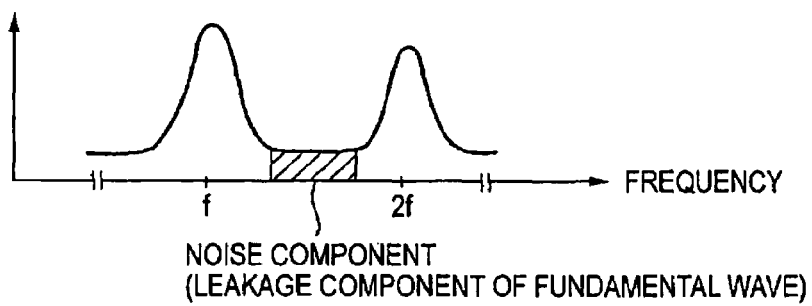
FIGS. 22A and 22B show parts of the spectra of reflected waves obtained in a case where an ultrasonic wave has been transmitted at 2 rates by the prior-art method, respectively.
Figure 22B:
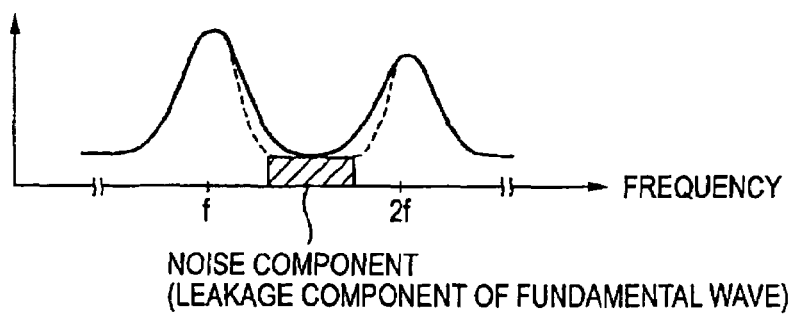

FIG. 22A shows part of the spectrum of reflected waves obtained by the transmission ultrasonic wave of the first rate in the case where the ultrasonic wave has been transmitted at 2 rates by the prior-art method (that is, without performing the specified control of a difference frequency component). Besides, FIG. 22B shows part of the spectrum of reflected waves obtained by the transmission ultrasonic wave of the second rate. As seen from FIGS. 22A and 22B, an echo signal generated by a motion in the temporal difference between the rates is superposed on the leakage component of a first fundamental wave as lies on the higher frequency side of the fundamental wave and the lower frequency side of the harmonic wave thereof.

Figure 22C:
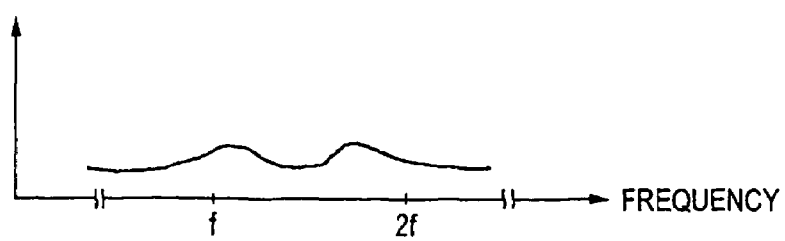
FIG. 22C shows a spectrum obtained by subtraction processing.

Besides, in a case where the signal of FIG. 22A is subtracted from the signal of FIG. 22B, a noise component (motion artifact) which is caused by the motion having arisen between the first and second rates remains as shown in FIG. 22C. In this case, the motion artifact appears about 10% of the signal which originates from the tissues and which includes the leakage component of the fundamental wave.

Figure 23A:
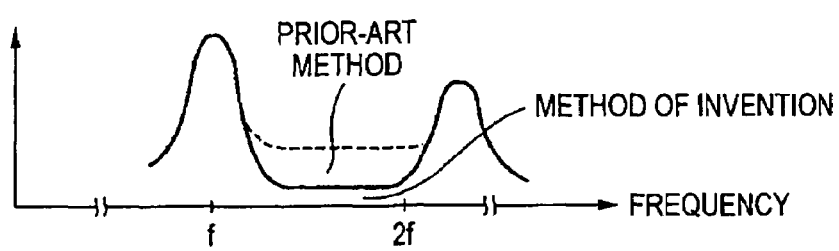
FIGS. 23A and 23B show parts of the spectra of reflected waves obtained in a case where an ultrasonic wave has been transmitted at 2 rates by a method according to an embodiment, respectively.
Figure 23B:
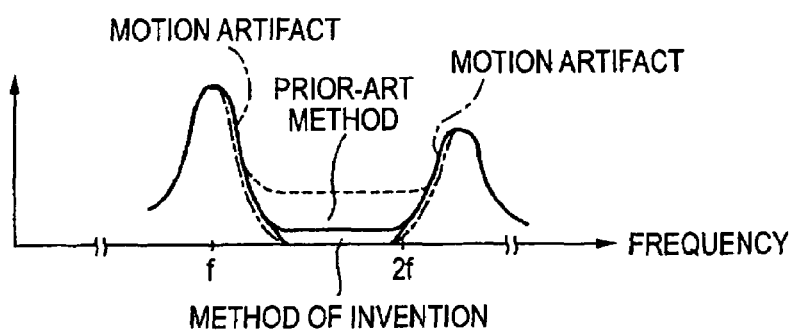

On the other hand, FIG. 23A shows part of the spectrum of reflected waves obtained by the transmission ultrasonic wave of the first rate in the case where the ultrasonic wave has been transmitted at the 2 rates by the method according to this embodiment. Besides, FIG. 23B shows part of the spectrum of reflected waves obtained by the transmission ultrasonic wave of the second rate. As seen from FIG. 23A, the leakage component of the fundamental wave is reduced relatively to the same in the prior art, owing to the weakening by the difference frequency component, and as seen from FIG. 23B, only the echo signal generated by the motion in the temporal difference between the rates appears on the higher frequency side of the first fundamental wave and on the lower frequency side of the harmonic wave.

Figure 23C:
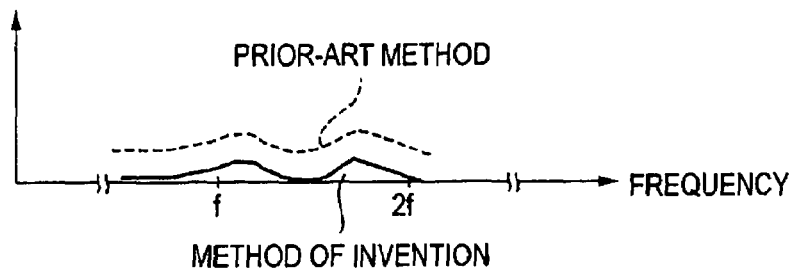
FIG. 23C shows a spectrum obtained by subtraction processing.

Besides, in a case where the signal of FIG. 23A is subtracted from the signal of FIG. 23B, a noise component (motion artifact) which is caused by the motion having arisen between the first and second rates remains as shown in FIG. 23C. In this case, the motion artifact appears about 10% of the signal which originates from the tissues and from which the leakage component of the fundamental wave has been removed. Accordingly, the motion artifact can be made lower than with the prior-art method.

As stated above, with the method according to this embodiment, the leakage component of the fundamental wave as included in the reception signal is first removed or reduced by the difference frequency component, and the subtraction processing between the rates is thereafter performed using the resulting reception signal so as to extract the contrast medium echo signal. Accordingly, the leakage component itself of the fundamental wave and the influence of the motion artifact on the leakage component of the fundamental wave can be eliminated, and the signal originating from the tissues can be removed at a high accuracy by the subtraction processing. As a result, the contrast medium echo component can be enhanced more relatively to the same in the prior art, and effective blood flow information can be imaged.

While the present invention has been thus far described in conjunction with embodiments, one skilled in the art can suggest various modifications and alterations within the category of the idea of the invention, and it is to be understood that the modifications and alterations fall within the scope of the invention. As indicated in items (1)-(3) by way of example below, the embodiments can be variously changed within the scope not departing from the subject matter of the invention.

(1) In each of the embodiments, there has been exemplified the case where the echo signal suitable for imaging is extracted by utilizing the difference frequency component generated on the basis of the two fundamental waves. It is also allowed, however, to adopt a configuration in which a similar operation is realized by utilizing a difference frequency component generated on the basis of two or more fundamental waves.

(2) In each of the embodiments, the frequency of the second fundamental wave whose frequency is higher in the two fundamental waves is controlled, thereby to control the frequency of the difference frequency component which is generated on the basis of the two fundamental waves. However, this does not intend any restriction, but it is also allowed to adopt a configuration in which the first fundamental wave of lower frequency is controlled in accordance with the frequency band of the fundamental waves to-be-used, thereby to control the frequency of the difference frequency component.

(3) In the first or second embodiment, it is also allowed to adopt a configuration in which transmissions at 2 rates with phases inverted by way of example are performed, and reception signals corresponding to the respective rates are added up, thereby to remove the fundamental wave components. In accordance with such a configuration, in the first embodiment, the second harmonic component to be imaged can be more enlarged by the superposition of the difference frequency component and the addition processing. Besides, in the second embodiment, the second harmonic wave which is, in principle, double larger can be obtained by the addition processing.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ultrasonic diagnostic equipment comprising:
   a transmission ultrasonic wave generation unit which generates a transmission ultrasonic wave that has, at least, a first frequency component, and a second frequency component at a frequency higher than that of the first frequency component, and which generates the transmission ultrasonic wave by controlling the frequency of at least one of the first and second frequency components so that, in a case of transmitting the transmission ultrasonic wave to a patient and receiving a reflected wave therefrom, a difference frequency component between the first frequency component and the second frequency component as is included in the reflected wave may interact with a second harmonic wave of the first frequency component, and also by controlling a phase difference between the first frequency component and the second frequency component to control the interaction;
   a transmission unit which transmits the transmission ultrasonic wave including the first frequency component and the second frequency component to the patient;
   a reception unit which receives the reflected wave of the transmission ultrasonic wave from the patient; and
   an image generation unit which generates an ultrasonic image on the basis of the reflected wave.

2. An ultrasonic diagnostic equipment as defined in claim 1,
wherein said transmission ultrasonic wave generation unit generates the transmission ultrasonic wave by controlling the phase of at least one of the first and second frequency components so that the second harmonic wave and the difference frequency component may become in phase.

3. An ultrasonic diagnostic equipment as defined in claim 2,
wherein said transmission ultrasonic wave generation unit:
sets a phase difference of the second frequency component relative to the first frequency component, at π in a case where the first frequency component and the second frequency component are of sine type; and
sets a phase difference of the second frequency component relative to the first frequency component, at 0 or 2π in a case where the first frequency component and the second frequency component are of cosine type.

4. An ultrasonic diagnostic equipment as defined in claim 1,
wherein said transmission ultrasonic wave generation unit generates the transmission ultrasonic wave by controlling the phase of at least one of the first and second frequency components so that the second harmonic wave and the difference frequency component may become opposite phases.

5. An ultrasonic diagnostic equipment as defined in claim 4,
wherein said transmission ultrasonic wave generation unit:
sets a phase difference of the second frequency component relative to the first frequency component, at 0 or 2π in a case where the first frequency component and the second frequency component are of sine type; and
sets a phase difference of the second frequency component relative to the first frequency component, at π in a case where the first frequency component and the second frequency component are of cosine type.

6. An ultrasonic diagnostic equipment as defined in claim 1,
wherein said transmission ultrasonic wave generation unit controls the frequency of the second frequency component to be lower than triple the frequency of the first frequency component, so that the difference frequency component may be superposed on the second harmonic wave on a lower frequency side of the second harmonic wave.

7. An ultrasonic diagnostic equipment as defined in claim 1,
wherein said transmission ultrasonic wave generation unit controls the frequency of the second frequency component to be, at least, equal to triple the frequency of the first frequency component, so that the difference frequency component may be superposed on the second harmonic wave on a higher frequency side of the second harmonic wave.

8. An ultrasonic diagnostic equipment as defined in claim 1,
wherein said transmission ultrasonic wave generation unit generates the transmission ultrasonic wave by controlling the phase of the second frequency component so that the difference frequency component may be superposed on the second harmonic wave on a lower frequency side and a higher frequency side of the second harmonic wave.

9. An ultrasonic image generation method comprising:
generating a transmission ultrasonic wave that has, at least, a first frequency component, and a second first frequency component, by controlling the frequency of at least one of the first and second frequency components so that, in a case of transmitting the transmission ultrasonic wave to a patient and receiving a reflected wave therefrom, a difference frequency component between the first frequency component and the second frequency component as is included in the reflected wave may interact with a second harmonic wave of the first frequency component, and also by controlling a phase difference between the first frequency component and the second frequency component to control the interaction;
transmitting the transmission ultrasonic wave to the patient;
receiving the reflected wave of the transmission ultrasonic wave from the patient; and
generating an ultrasonic image on the basis of the reflected wave.

* * * * *